United States Patent
Stefely et al.

(10) Patent No.: US 6,416,742 B1
(45) Date of Patent: Jul. 9, 2002

(54) MEDICINAL AEROSOL SOLUTION FORMULATION WITH BIOCOMPATIBLE POLYMER

(75) Inventors: James S. Stefely, Woodbury; David W. Schultz, Pine Springs; Luke E. Schallinger, Maplewood; Craig A. Perman, Woodbury; Chester L. Leach, Lake Elmo; Daniel C. Duan, St. Paul, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/634,406

(22) Filed: Aug. 9, 2000

Related U.S. Application Data

(62) Division of application No. 08/797,803, filed on Feb. 7, 1997, now Pat. No. 6,126,919.

(51) Int. Cl.$^7$ .................................................. A61K 9/12
(52) U.S. Cl. ........................................... 424/45; 424/46
(58) Field of Search ............................ 424/45, 46, 426

(56) References Cited

U.S. PATENT DOCUMENTS

| | | |
|---|---|---|
| 2,457,238 A | 12/1948 | Hunter et al. |
| 3,079,299 A | 2/1963 | Heilig |
| 3,755,558 A | 8/1973 | Scribner |
| 3,773,919 A | 11/1973 | Albert et al. |
| 3,816,612 A | 6/1974 | Schmidt et al. |
| 3,887,699 A | 6/1975 | Yolles |
| 3,933,825 A | 1/1976 | Fiscella et al. |
| 4,010,196 A | 3/1977 | Tsuk |
| 4,011,312 A | 3/1977 | Reuter et al. |
| 4,683,288 A | 7/1987 | Tanaka et al. |
| 4,728,721 A | 3/1988 | Yamamoto et al. |
| 4,732,763 A | 3/1988 | Beck et al. |
| 4,801,739 A | 1/1989 | Franz et al. |
| 4,849,228 A | 7/1989 | Yamamoto et al. |
| 4,851,211 A | 7/1989 | Adjei et al. |
| 4,869,899 A | 9/1989 | Burghart et al. |
| 4,897,268 A | 1/1990 | Tice et al. |
| 4,981,850 A | 1/1991 | Wade |
| 4,997,643 A | 3/1991 | Partain et al. |
| 5,236,702 A | 8/1993 | Ritter et al. |
| 5,300,255 A | 4/1994 | Campbell et al. |
| 5,302,693 A | 4/1994 | Stricker et al. |
| 5,384,133 A | 1/1995 | Boyes |
| 5,399,353 A | 3/1995 | Bartnik et al. |
| 5,424,063 A | 6/1995 | Cardin et al. |
| 5,478,921 A | 12/1995 | Roby et al. |
| 5,480,868 A | 1/1996 | Kamei et al. |
| 5,482,717 A | 1/1996 | Fues et al. |
| 5,536,445 A | 7/1996 | Campbell et al. |
| 5,538,721 A | 7/1996 | Babcock et al. |
| 5,567,431 A | 10/1996 | Vert et al. |
| 5,569,450 A | 10/1996 | Duan et al. |
| 5,594,091 A | 1/1997 | Igari et al. |
| 5,618,911 A | 4/1997 | Kimura et al. |
| 5,631,015 A | 5/1997 | Bezwada et al. |
| 5,633,002 A | 5/1997 | Stricker et al. |
| 5,633,022 A | 5/1997 | Stricker et al. |
| 5,648,096 A | 7/1997 | Gander et al. |
| 5,653,992 A | 8/1997 | Bezwada et al. |
| 5,665,394 A | 9/1997 | Igari et al. |
| 5,672,659 A | 9/1997 | Shalaby et al. |
| 5,871,771 A | 2/1999 | Zierenberg et al. |
| 5,874,064 A | 2/1999 | Edwards et al. |

FOREIGN PATENT DOCUMENTS

| | | |
|---|---|---|
| CA | 2017851 | 11/1990 |
| DE | 39 16 020 | 11/1990 |

(List continued on next page.)

OTHER PUBLICATIONS

H.O. Alpar et al., "Preparation and Characteristics of Gentamicin–Containing Poly (Lactide–Co–Glycolide) Microspheres for Lung Targeting", *J. Pharmacy & Pharmacology*, 44, 1082 (Dec. 1992).

M. Asano et al., "Biodegradability of a hot–pressed poly(lactic acid) formulation with controlled release of LH–RH agonist and its pharmacological influence on rat prostate", *Makromol. Chem. Rapid Commun.*, 6, 509–513 (1985).

M. Asano et al., "In vivo controlled release of luteninzing hormone–releasing hormone agonist from poly (DL–lactic acid) formulations of varying degradation pattern", *Int'l J. Pharm.*, 67, 67–77 (1991).

D. Bendix, "Some Remarks on the Broad Molecular Weight Distribution of Poly(D,L–Lactide–co–Glycolides) with Low INH Viscosities", *Proced. Intern. Symp. Control. Rel. Bioact. Mater.*, 16, 505–506 (1989).

S. Berge et al., "Pharmaceutical Salts," *J. Pharm. Sci.*, 66, 1–19 (1977).

R. Bodmeier et al., "The effect of the addition of low molecular weight poly(DL–lactide) on drug release from biodegradable poly(DL–lactide) drug delivery systems", *Int'l. J. Pharm.*, 51, 1–8 (1989).

(List continued on next page.)

*Primary Examiner*—Raj Bawa
(74) *Attorney, Agent, or Firm*—Ted K. Ringsred; MarySusan Howard; Robert W. Sprague

(57) ABSTRACT

Methods, compounds, and medicinal formulations utilizing biocompatible polymers for delivery of a drug, particularly for solubilizing, stabilizing and/or providing sustained release of drug from topical, implantable, and inhalation systems. Many of the methods, compounds, and medicinal formulations are particularly suitable for oral and/or nasal inhalation and use polymers of the formula —[X—$R^1$—C(O)]— wherein each $R^1$ is an independently selected organic group that links the —X— group to the carbonyl group, and each X is independently oxygen, sulfur, or catenary nitrogen.

40 Claims, No Drawings

FOREIGN PATENT DOCUMENTS

| | | |
|---|---|---|
| EP | 0 172 636 | 3/1986 |
| EP | 0 330 180 | 8/1989 |
| EP | 0 368 253 | 5/1990 |
| EP | 368 571 | 5/1990 |
| EP | 0 372 777 | 6/1990 |
| EP | 400 522 | 12/1990 |
| EP | 463 194 | 1/1992 |
| EP | 468 199 | 1/1992 |
| EP | 0 521 455 | 1/1993 |
| EP | 0 534 731 | 3/1993 |
| EP | 0 601 799 | 6/1994 |
| EP | 0 605 578 | 7/1994 |
| EP | 0 668 073 | 8/1995 |
| GB | 2 166 652 | 5/1986 |
| GB | 2 234 896 | 2/1991 |
| JP | 95-316272 | 12/1995 |
| JP | 95-316273 | 12/1995 |
| JP | 9-59218 | 3/1997 |
| JP | 9-124778 | 5/1997 |
| WO | 87/03197 | 6/1987 |
| WO | 92/15340 | 9/1992 |
| WO | 94/15587 | 7/1994 |
| WO | 94/21228 | 9/1994 |
| WO | 94/21229 | 9/1994 |
| WO | 95/05153 | 2/1995 |
| WO | 95/15151 | 6/1995 |
| WO | 96/03983 | 2/1996 |
| WO | 97/40085 | 10/1997 |
| WO | 88/09185 | 12/1998 |

OTHER PUBLICATIONS

A. Carrio et al., "Preparation and degradation of surfactant--free PLAGA microspheres", *J. Controlled Release*, 37, 113–121 (1995).

N. Celebi et al., "The preparation and evaluation of salbutamol sulphate containing poly(lactic acid–co–glycolic acid) microspheres with factorial design–based studies", *Int'l J. Pharm.*, 136, 89–100 (1996).

P.P. DeLuca et al., "Biodegradable Polyesters for Drug and Polypeptide Delivery", *Polymeric Delivery Systems;* ACS; Chapter 4, 53–77 (1993).

G.A. Digenis et al., "Peptidyl Carbamates as Novel Elastase Inhibitos: Lung Delivery by Polyglycolic Acid Microspheres", *Pharm. Res.*, 3, Abstract No. 85 (1986).

M. Dittrich et al., "Purification of biodegradable polymers and oligomers of aliphatic hydroxy acids", Abstract of Czech Patent No. CZ 278181 (Sep. 15, 1993) CA122(16):188468y.

S.E. Dunn et al., "Studies on In–Vitro Uptake by Kupffer Cells and the In–Vivo Biodistribution of a Range of Novel Polymeric Colloids", *J. Pharmacy & Pharmacology*, 44, 1082 (1992).

N. Erden et al., "Factors influencing release of salbutamol sulphate from poly(lactide–co–glycolide) microspheres prepared by water–in–oil–in–water emulsion technique", *Int'l J. Pharm.*, 137, 57–66 (1996).

H. Fukuzaki et al., "Synthesis of Copoly (D,L–Lactic Acid) with Relatively Low Molecular Weight and In Vitro Degradation", *Eur. Polym., J.*, 25, 1019–1026 (1989).

B. Guiziou et al., "Investigation of in–vitro release characteristics of NSAID–loaded polylactic acid microspheres", *J. Microencapsulation*, 13, 701–708 (1996).

P.K, Gupta et al., "Development and Characterization of Aerosol Formulations of Biodegradable Microspheres for Targeted Delivery to the Lungs", *Pharm. Res.*, 7, Abstract No. PT 6055 (1990).

K. Jamshidi et al., "Thermal characterization of polylactides", *Polymer*, 29, 2229–2234 (Dec. 1988).

I. Kaetsu et al., "Biodegradable Implant Composited for Local Therapy", *J. Controlled Release*, 6, 249–263 (1987).

K. Kimura et al., "Acid terminal–blocked poly(lactic acid) with good hydrolysis resistance", abstract of Japanese Patent No. 07316273 (Dec. 5, 1995) CA124(16):203400g.

K, Kimura et al., "Polylactic acid and/or their copolymers", abstract of Japanese Patent No. 07316272 (Dec. 5, 1995) CA124(12):14775u.

M. Kulkarni et al., "Characterization of Aerosol Formulations of Biodegradable Microspheres", *Pharm Res.* 8, Abstract No. PT 6013 (Oct. 1991).

M. Kulkarni et al., "Formulation of PLCA Microspheres as a Suspension Metered Dose Inhaler: Effect of Formulation Variables", *Pharm Res.* 11, Abstract No. PDD 7141 (1994).

M. Kulkarni et al., "In–Vitro and In–Vitro Testing of Indium Labeled Poly (D,L–LactideCo–Glycolide) Microsphere Metered Dose Inhalers", *Pharm Res*, 11, Abstract No. PDD 7149 (1994).

M. Kulkarni et al., "Stability of PLGA Microsphere Metered Dose Inhaler Formulations", *Pharm. Res.*, 11, Abstract No. PDD 7150 (1994).

Y–L. Lai et al., "Sustained Bronchodilation with Isoproterenol Poly(Glycolide–co–Lactide) Microspheres", *Pharm. Res.*, 10, 119–125 (1993).

J.G.P. Lim et al., "Studies of Hydrophobic Microspheres for Controlled Pulmonary Drug Delivery", *J. Pharmacy & Pharmacology*, 41, 8P (1989).

L. Masinde et al., "Nebulization of Poly (Lactic Acid) Microspheres From Aqueous Suspension", *Pharm. Res.*, 8, Abstract No. PT6150 (1991).

L. Masinde et al., "Aerosolized Aqueous Suspensions of Poly(L–Lactic Acid) Microsphere", *Int'l. J. Pharm*, 100, 123–131 (1993).

S. Nagata et al., "Pharmaceutical dosage form design of copoly(lactic/glycolic acid) microspheres. Mechanism of in vitro release of gentamicin", *Yakugaku Zasshi*, 114, 1005–1014 (1994). CA 122:196760.

K. Nakamura et al., "Controlled release of poly–D–L–lactic acid containing bleomycin", *Anti–Cancer Drugs*, 6, 483–487 (1995).

K.H. Oh et al., "Plasticization of biodegradable films and microspheres with low molecular weight polymeric fractions", *J. Pharm. Sci.*, 76, Abstract No. N 03–W–(1987).

E.A. Poyner et al., "A comparative study on the pulmonary delivery of tobramycin encapsulated into liposomes and PLA microspheres following intravenous and endotracheal delivery", *J. Controlled Release*, 35, 41–48 (1995).

S. Ramanathan et al., "Controlled Release of Amiodarone from Poly L–Lactic Acid Microspheres", *Pharm. Res.*, 10, Abstract No. PDD 7400 (1993).

K.M. Scholsky et al., "Characterization of Copolymers Fractionated Using Supercritical Fluids", *J. Applied Polymer Science*, 33, 2925–2934 (1987).

J.W. Tom et al., "Precipitation of Poly(L–lactic acid) and Composite Poly(L–lactic acid)–Pyrene Particles by Rapid Expansion of Supercritical Solutions", *J. Supercritical Fluids*, 7, 9–29, (1994).

T–Z. Tzou et al., "Comparing the Aerodynamic Particle Size of MDIs Measured by the Quartz Crystal Microbalance Cascade Impactor and the Andersen Cascade Impactor", *Pharm. Res.,* 12, Abstract No. PT 6179 (1995).

R. Wada et al., "Lactic Oligomer Microspheres Containing an Anticancer Agent for Selective Lymphatic Delivery: I. In Vitro Studies", *J. Bioactive and Compatible Polymers,* 3, 126–136 (1988).

R. Wada et al., "New biodegradable oligoesters for pharmaceutical application", *J. Biomater. Sci. Polym. Ed.,* 7, 715–725 (1996).

D.A. Edwards et al., "Large Porous Particles for Pulmonary Drug Delivery", *Science,* 276, 1868–1871 (1997).

M.M. El–Baseir et al., "Preparation and Subsequent Degradation of Poly(l–lactic acid) Microspheres Suitable for Aerosolisation: A Physico–Chemical Study", *Int. J. Pharm.,* 151, 145–153 (1997).

D.N. Leff, "Penn State, MIT Prove Large, Porous Aerosol Drugs Deliver Superior Therapy", *Bioworld Today,* 8, No. 119, pp. 1, 3 (1997).

T. Niwa, "Aerosolization of Lactide/Glycolide Copolymer (PLGA) Nanospheres for Pulmonary Delivery of Peptide–drugs", *Yakugaku Zasshi,* 115, No. 9, pp. 732–741 (1995).

Y. Ogawa, "Injectable Microcapsules Prepared with Biodegradable Poly(α–hydroxy) Acids for Prolonged Release of Drugs", *J. Biomater. Sci. Polymer Edn.,* 8, No. 5, pp. 391–409 (1997).

V.A. Philip et al., "Effect of Surface Treatment on the Respirable Fractions of PLGA Microspheres Formulated for Dry Powder Inhalers", *Int. J. Pharm.,* 151, 165–174 (1997).

V.A. Philip et al., "In Vitro and In Vivo Respirable Fractions of Isopropanol Treated PLGA Microspheres Using a Dry Powder Inahler", *Int. J. Pharm.,* 151, 175–182 (1997).

H. Sato et al., "Pharmacokinetic Study of Taxol–Loaded Poly(lactic–co–glycolic acid) Microspheres Containing Isopropyl Myristate after Targeted Delivery to the Lung in Mice", *Biol. Pharm. Bull.,* No. 12, 1596–1601 (1996).

D.A. Edwards et al., "Large Porous Aerosols for Pulmonary Drug Delivery", *Proceed. Int'l Symp. Control. Rel. Bioact. Mater.,* 24, 67–68 (1997).

J. Hanes et al., "Porous Dry–Powder PLGA Microspheres Coated with Lung Surfactant for Systemic Insulin Delivery Via the Lung", *Proceed Int'l Symp. Control. Rel. Bioact. Mater.,* 24, 57–58 (1997).

J. Hanes et al., "Porous Poly(D,L–Lactic–CO–Glycolic Acid) Microsphere Degradation and Release of Macromolecules", *Proceed Int'l. Symp. Control. Rel. Bioact. Mater.,* 24, 1027–1028 (1997).

Wang, Nuo, et al, "Stabilization of Aspirin by Using a Lactic/Glycolic Acid Oligomer", American Chemical Society, papers presented at Las Vegas meeting, vol. 38, No. 2, p. 568–569, (1997).

Wang, Nuo, et al, Synthesis, Characterization, Biodegradation, and Drug Delivery Application of Biodegradable Lactic/Glycolic Acid Oligomers: I. Synthesis and Characterization, *J. Biomater. Sci. Polymer Edn,* vol. 8, No. 12, pp. 905–917 (1997).

Wang, Nuo, et al., Synthesis, characterization, Biodegradation, and Drug–Delivery Application of Biodegradable Lactic/Glycolic Acid Oligomers: Part II. Biodegradation and Drug Delivery Application, *J. Biomater. Sci. Polymer Edn,* vol. 9, No. 1, pp. 75–87—(1997).

MEDICINAL AEROSOL SOLUTION FORMULATION WITH BIOCOMPATIBLE POLYMER

This is a division of application Ser. No. 08/797,803 filed Feb. 7, 1997, now U.S. Pat. No. 6,126,919 patented Oct. 3, 2000.

The present invention relates to the use of relatively low molecular weight biocompatible polymeric compounds for pharmaceutical drug delivery formulations, and, in particular, to the use of such compounds as drug solubilizing and drug stabilizing aids and/or to provide sustained release of drug.

BACKGROUND OF THE INVENTION

Biodegradable polymers have long been examined for their use in providing sustained release of drugs and have also been used to make biodegradable medical products. For example, polymeric esters of selected hydroxycarboxylic acids or their derivatives (e.g., lactic acid, glycolic acid, p-dioxanone, etc.) are known to be highly biocompatible with, and biodegradable in, the human body. Such polymers are degraded into their constituent hydroxycarboxylic acids, which are metabolized and eliminated from the body, over periods typically ranging from several weeks to several years. Consequently, compounds of this type have been utilized for such things as degradable sutures, preformed implants, and sustained release matrices.

However, the biodegradable polymers in use for such purposes typically have average molecular weights of greater than 2000 and often as high as 50,000 to 250,000 (all molecular weights referred to herein are in daltons). This results in biodegradation rates that are generally too slow for situations requiring frequent application and/or where a biological half-life of less than a week down to several hours is desired (e.g., topical application to a wound or for inhalation therapy). Certain relatively low molecular weight polymers having a number-average molecular weight under about 1800 may have sufficiently short biodegradation times for many such purposes, but have generally not been deemed suitable for most sustained release drug delivery systems. This is at least in part because the physical characteristics of these relatively low molecular weight polymers have been regarded as unsuitable for many conventional drug delivery formats. For example, polylactic acids having a number-average molecular weight of less than about 1000 with a normal molecular weight distribution (i.e., a distribution that is substantially unchanged from that obtained via polymerization), typically having a polydispersity (i.e., the ratio of the weight-average to number-average molecular weights) of greater than about 1.8, tend to have a glass transition temperature (Tg) below room temperature, which is about 23° C., and are generally soft, waxy, or tacky materials. Such materials are not generally suitable for making conventional preformed, solid, drug-containing structures, such as microspheres, for sustained drug release because the low Tg prevents the material from maintaining its physical integrity. Also, the release rate of drug from, and percent loading of drug into, conventional low molecular weight biodegradable systems have not generally been considered sufficient to be useful for most drug delivery systems. Accordingly, formulations and methods of utilizing biocompatible, and preferably biodegradable, polymers to provide relatively short term sustained release of drugs would be highly desirable.

One particular area where sustained release is extremely useful, and yet has been difficult to achieve satisfactorily, is in the context of drug inhalation therapy, such as with metered dose inhalers (MDIs). Drugs used for localized pulmonary administration, for example bronchodilators, are usually limited in their efficacy by the necessity for frequent administration. This is typically due to the rapid dissolution, absorption, and metabolism of the drugs in the lung. Many attempts have been made to provide sustained release of drugs to the lung, as well as other locations, by entrapping or encapsulating the drug in preformed, biodegradable microspheres.

However, there are serious drawbacks with using preformed microspheres. First, it has generally been necessary to use polymers with a number-average molecular weight of at least about 1800, and usually higher, so that the Tg is high enough for the particles to remain discrete, or at least separable, prior to use. As noted above, polymers of too high molecular weight will typically degrade too slowly to be useful in inhalation therapy because of the tendency for higher molecular weight materials to collect and build up in the lung parenchyma upon continued use. Second, the production of preformed microspheres is often difficult, inefficient, costly, and may involve the use of materials which are physiologically and/or environmentally hazardous. Despite efforts to improve the processes, there are often problems with, for example, low and inefficient drug entrapment, aggregation of particles, wide distributions of particle sizes, and the presence of nonparticulate materials.

Hence, there is a substantial need for means of making microparticles that are suitable for pulmonary drug delivery and will not accumulate in the lung, and, even more preferably, for means of providing sustained release of drug without requiring the use of preformed microspheres at all.

Another important issue relating to medicinal aerosol formulations such as in MDIs relates to whether the drug is dissolved in the formulation or present as a micronized suspension of particles. Although there are advantages to using aerosol formulations where the drug is in solution, most commercially available MDIs have the drug suspended in the propellant as a micronized dispersion. This is because in most cases the drug either is not sufficiently soluble in the formulation to form a stable solution or, if soluble, the drug is too chemically unstable in its dissolved form. Accordingly, there is also a substantial need for biocompatible compounds that act as solubilizing aids and/or chemical stabilizers for drug in medicinal aerosol formulations.

U.S. Pat. No. 5,569,450 (Duan et al.) discloses that biocompatible oligomers such as oligohydroxycarboxylic acids are useful as dispersing aids to help maintain particles as a suitable suspension. However, it does not disclose formulations of such compounds providing sustained drug release or as a drug solubilizing and/or stabilizing aid.

In other, non-inhalation contexts, biocompatible polymers have been used for various therapeutic systems, such as spray-on skin covering films which may have a drug included. Such systems, however, are generally not deemed to have both suitable physical and biological/degradation characteristics for most sustained release drug delivery applications.

SUMMARY OF THE INVENTION

The methods, compounds, and medicinal formulations of the present invention provide broadly applicable means for delivery of a drug. They are particularly useful for drug solubilization and chemical stabilization, as well as for providing sustained release of drug from a drug delivery system, such as topical, implantable, and inhalation systems.

Additionally, means are provided for improving the physical and degradation characteristics of biodegradable polymers and also for forming drug-polymer medicinal salts. Many of the methods, compounds, and medicinal formulations are particularly useful for oral and/or nasal drug delivery, such as by inhalation from a metered dose inhaler.

Biocompatible Polymers

All of the formulations of the present invention utilize one or more biocompatible, and preferably biodegradable, polymeric compounds. As used herein, "polymer" and "polymeric" are, unless otherwise indicated, intended to broadly include homopolymers and block/random copolymers (and oligomers) including a chain of at least three or more monomer structural units formed by polymerization reactions (e.g., condensation or ring-opening polymerization). Preferred biocompatible polymers are biodegradable and are preferably formed by a condensation type polymerization. For some preferred embodiments, the biocompatible polymers are homopolymers, while for others they are copolymers. Preferably, the repeating structural units contain amide units, ester units, or mixtures thereof Preferred such biocompatible polymers include at least one chain of units of the formula $-[X-R^1-C(O)]-$ wherein: each $R^1$ is an independently selected organic group that links the X group to the carbonyl group; and each X is independently oxygen, sulfur, or catenary nitrogen. Such compounds can include chains having different $R^1$ groups, although for certain embodiments each $R^1$ moiety is the same. The preferred X group is oxygen. Particularly preferred biocompatible polymers are relatively low molecular weight polylactic acids (PLAs). One reason they are preferred is because lactic acid is well known to be endogenous in humans, highly biocompatible and, therefore, desirable from a regulatory approval standpoint. Other biocompatible polymers are also useful in methods and formulations according to the present invention. For example, homopolymers and copolymers of lactic acid, glycolic acid, trimethylene carbonate, hydroxybutyric acid, and p-dioxanone have all been found to be particularly useful in various embodiments of the present invention. In particular, polydioxanone and polylactic-co-glycolic acids are well established as being biocompatible and, accordingly, are also good candidates from a regulatory approval standpoint.

It is also sometimes preferred that one or more chains of the biocompatible polymer can be capped at one end or both ends by either a monovalent, divalent, or polyvalent organic moiety (each valence of the capping group being independently bonded to a chain) that does not contain hydrogen atoms capable of hydrogen bonding, or by a monovalent, divalent, or polyvalent ionic group, or a group that does contain hydrogen atoms capable of hydrogen bonding. The choice of end groups can modify the performance of the polymer, either in the formulation or biologically, and the preferred choice will depend on the particular intended application of the invention. One preferred polymer end cap is an acetyl group.

Also, it should be pointed out that the various preferred amounts, molecular weights, and ranges set forth below are given for general guidance and are based primarily on poly-L-lactic acids, so this should be taken into account when considering other polymers for use in the present invention. For example, polyglycolic acids typically hydrolyze more quickly, exhibit higher degrees of crystallinity, and have higher melting points than polylactic acids. This should be taken into account when considering such things as what polymer to use to achieve the particular sustained release or formulation characteristics desired. Moreover, in the case of polylactic acids, the naturally occurring L form is frequently preferred over the D or DL forms because it is endogenous in humans. However, due to the amorphous nature of the DL compounds, there are applications where the DL compounds (i.e., mixtures of L and D isomers), are also sometimes preferred.

Low Polydispersity Compositions

A first aspect of the invention, which may or may not be used in conjunction with other aspects discussed below, relates to improving the physical and degradation characteristics of biodegradable polymers. As noted above, conventional polymer compositions with the highly desirable property of relatively rapid biodegradation typically also exhibit poor physical characteristics. They tend to be sticky, waxy, and generally unable to maintain the physical integrity of articles formed therewith (e.g., microspheres anneal together, rods conform to their container shape, etc.). However, it has been found that, contrary to conventional understanding, it is in fact possible to achieve the highly desirable combination of relatively rapid biodegradation and good physical characteristics with a relatively low molecular weight biodegradable polymer. This surprising effect is accomplished by limiting the polydispersity (i.e., the ratio of weight-average to number-average molecular weight) of the polymer to a relatively narrow range as compared to the normally occurring distribution (i.e., the molecular weight distribution that occurs normally from the conventional polymerization methods). It is hypothesized that this unexpected improvement is the result of several factors: reducing the amount of the slowly degrading high molecular weight component of the polymer reduces the polymer's overall biological half-life; while reducing the amount of the plasticizing low molecular weight component of the polymer raises the Tg of the material. Also, removal of the low molecular weight component seems to "sharpen" the transition between the flowing and non-flowing phases, i.e., it raises the Tg onset temperature (the point where tackiness and flow begins to occur) closer to the mid-point Tg. Thus, by limiting the polydispersity of the biodegradable polymer, the degradation characteristics can be improved without sacrificing, and perhaps improving, the physical characteristics of the composition. For example, by reducing the polydispersity of the polymer composition, a generally hard, non-tacky, and relatively rapidly degrading material can be produced. With this aspect of the present invention it is thus possible to make relatively low molecular weight drug-containing medicinal compositions that have both more rapid biodegradation and improved handling characteristics. This has potential application in virtually any context where a relatively rapidly biodegrading polymer is desired. For example, it can be used to make preformed drug-containing microparticles and implants. As discussed below, narrow polymer polydispersity can also provide benefits when dissolved in an MDI formulation to provide controlled release, solubilization and/or chemical stabilization of a drug.

In order to provide rapid biodegradation and good physical characteristics, the biodegradable polymer preferably has a number-average molecular weight of no greater than about 1800, and more preferably no greater than 1500 (and generally no less than about 700), and a polydispersity of less than about 1.3, more preferably less than about 1.2, and most preferably less than about 1.15. The biodegradable polymer preferably comprises at least one chain of units of the formula $-[O-R^1-C(O)]-$ wherein each $R^1$ is an independently selected organic group that links the oxygen atom to the carbonyl group. More preferably, the biodegradable polymer is polylactic acid, polyglycolic acid, or polylacticco-glycolic acid; and most preferably, it is poly-L-lactic acid. Some examples of uses for such biodegradable polymers having a relatively narrow molecular weight distribution include preformed drug-containing powders and particles (e.g., microspheres), such as used in dry powder inhalation systems, nebulizers, injection formulations, topical sprays, and suspension type MDI aerosol formulations, as well as subcutaneous implants, drug-delivery dental packs, and other drug-delivery systems. Polymers having such a relatively narrow molecular weight distribution can be prepared by any suitable means for limiting polydispersity. One preferred technique is to use a supercritical fluid, such as carbon dioxide, to fractionate the polymer. This useful technique is applicable to the biocompatible polymers described herein, as well as to other polymers in general.

Drug Solubilizing and/or Stabilizing

In another important aspect of the invention, biocompatible polymers are dissolved in medicinal formulations in order to help solubilize and/or chemically stabilize a drug. One preferred embodiment of this aspect of the invention is a medicinal formulation suitable for nasal and/or oral inhalation, such as from an MDI, that includes a propellant, a biocompatible condensation-type polymer, preferably comprising at least one chain of units of the formula —[X—$R^1$—C(O)]— wherein: each $R^1$ is an independently selected organic group that links the X group to the carbonyl group; and each X is independently oxygen, sulfur, or catenary nitrogen, and a therapeutically effective amount of a drug substantially completely dissolved in the formulation. Surprisingly, the biocompatible polymer, which is also substantially completely dissolved in the formulation, acts as a solubilizing aid and/or as a chemical stabilizing aid for many drugs. This is important because, as noted above, many drugs are not sufficiently soluble in aerosol formulations or, if soluble, are chemically unstable in their dissolved form. Optionally, a cosolvent may also be present, which may help solubilize either the drug, the biocompatible polymer, or both. Other excipients may also be included.

It is also preferred in this aspect of the invention, although not required, that the biocompatible polymer have a relatively narrow molecular weight distribution, i.e., polydispersity of less than about 1.8, preferably less than about 1.4, and more preferably less than about 1.2. This helps to prevent the inclusion of the larger polymers which could accumulate in the lung over time due to repeated dosing. It also can allow a greater amount of the polymer to be completely dissolved in an aerosol formulation, which may be particularly important when a polymer is being used as a drug solubilizing aid because such use can require substantial amounts of polymer to be dissolved (e.g., 1% or more of the formulation by weight). For example, poly-L-lactic acid shows improved solubility in hydrofluorocarbon (HFC) propellants when the polydispersity is reduced.

Sustained Release

In another separate but related aspect of the invention, it has been found that medicinal formulations using the biocompatible polymers of the present invention are highly useful in providing sustained release of a drug to the body. Such formulations include a drug and a sufficient amount of biocompatible (preferably, biodegradable) polymer which when delivered is associated with the drug (i.e., drug entrapped/encapsulated in a polymer matrix or, described below, as a drug-polymer salt,) so as to provide for such sustained release of the drug as the polymer degrades and the drug is released. This is useful in many drug delivery contexts, such as solid and semi-solid implants and microspheres, as well as for liquid injection formulations and topical sprays. However, it is particularly useful and surprising in the context of medicinal aerosol formulations, such as for oral and/or nasal inhalation from a metered dose inhaler Such sustained release aerosol formulations include drug and a sufficient amount of biocompatible polymer dissolved in a propellant to provide sustained release of the drug when inhaled, and may also include a cosolvent and other excipients. The drug may be in the form of a micronized suspension or substantially completely dissolved in the formulation. The biocompatible polymer preferably comprises at least one chain of units containing amide and/or ester groups. Preferably, the biocompatible polymer comprises at least one chain of units of the formula —[X—$R^1$—C(O)]— wherein: each $R^1$ is an independently selected organic group that links the X group to the carbonyl group; and each X is independently oxygen, sulfur, or catenary nitrogen.

It is particularly surprising to discover that when such biocompatible (preferably biodegradable) polymers are substantially completely dissolved in sufficient quantities relative to the drug in, for example, medicinal aerosol formulations, and administered to the body the drug is released in a highly desirable sustained manner over a period ranging, for example, from about 30 minutes to a day or more. The time period for release of the drug depends upon many factors including, for example, the amount, type, and molecular weight of the biocompatible polymer used, and the chemical and physical nature of the drug. The amount of polymer that will be sufficient to provide a desired sustained release profile may be determined on a case-by-case basis with little difficulty. In many situations, the polymer will comprise at least about 1% of the formulation to provide suitable sustained release, although this will depend on the polymer used and the amount, type and physical and chemical form of the drug. The polymer will generally be present in an amount of at least four times, and often 10 to 100 times, the amount of the drug on a weight to weight basis. In the case of suspension aerosol formulations, where the drug is present as micronized particles, the amount of biocompatible polymer necessary to provide sustained release is generally substantially more than that which would normally be used as a dispersing aid in, for example, the context of U.S. Pat. No. 5,569,450.

Moreover, although it may be preferred to use biocompatible polymers having, as described above, a relatively narrow molecular weight range (i.e., with a polydispersity of less than about 1.8 and preferably less than about 1.4, and most preferably less than about 1.2), it is not required according to all aspects of the invention, particularly in the sustained release formulations. For example, when poly-L-lactic acids of normal polydispersity are used in a formulation for pulmonary delivery, it is preferred that the number-average molecular weight of the polymer be no greater than about 800, and more preferably no greater than about 600. Otherwise, depending upon the frequency of administration, the higher molecular weight component present can accumulate in the lung. Additionally, normal polydispersity poly-L-lactic acids with molecular weights greater than about 800 may exhibit partial insolubility (depending on the weight percentage, propellant used, and the presence of co-solvents or other excipients) of the highest molecular weight fraction of the polymer. However, when poly-DL-lactic acids are used, such limitations are not generally encountered. When narrow molecular weight range poly-L-lactic acids (i.e., those having a polydispersity of less than about 1.8 and preferably less than about 1.4, and most preferably less than about 1.2) are used, however, the number-average molecular weight is preferably no greater than about 1300, and more preferably, for most applications, no greater than about 1000. For poly-DL-lactic acid, although solubility is generally not a problem, it is nonetheless desirable to use the lower polydispersity polymer due to the more rapid degradation. The molecular weight and polydispersity can be relatively higher in cases where frequent dosing or rapid bioabsorption are less important (e.g., vaccine or nasal delivery). One skilled in the art will recognize that these parameters will vary with each monomer type used. The choice of polymer used will also be based on the ability of the polymer, when delivered, to incorporate the drug into a matrix or as a salt (discussed below) and release it in a controlled manner. This depends on such factors as the polymer molecular weight, polydispersity, tendency toward crystallization, and specific functionality, as well as the nature of the drug and the form it is in (e.g. dissolved or suspended).

Thus, one can adjust the system according to the particular requirements of the delivery system. For example, where it is desired to provide a therapeutic drug inhalation system requiring only a single dose per day, the biocompatible polymer amount, average molecular weight, polydispersity, and other factors will preferably be selected so that the drug is controllably released, and substantially all of the polymer biodegraded (such that the polymer matrix material is substantially undetectable at the delivery site), over about a 24 hour period, and in some cases preferably over about a 12 hour period. This can typically be accomplished using, for example, poly-L-lactic acid having an average molecular weight of about 1000 and a polydispersity of about 1.2, although these and other various factors, such as the amount of polymer used, and selection of co-monomers (e.g., use of L and D isomers, glycolic acid, etc.), can be adjusted as required for a particular situation.

Also, significantly, the medicinal aerosol formulations described herein do not tend to form films, the presence of which would be highly undesirable in the pulmonary tract. Rather, they form discrete particles spontaneously upon the formulation exiting the aerosol canister valve (for example, from a metered dose inhaler). This aspect of the invention is important both in the context of providing sustained release microparticles, and for providing inhalable microparticles which are not for sustained release. Thus, there is also provided a simple method of forming discrete particles of a medicinal aerosol formulation, which is broadly applicable, cost effective, and, when a suitable propellant is used, environmentally friendly. The method includes the following steps: preparing a medicinal formulation by combining components comprising a propellant, a biocompatible polymer substantially completely dissolved in the formulation, a therapeutically effective amount of a drug (preferably, substantially completely dissolved in the formulation), and optionally with a cosolvent and/or other excipient; placing the medicinal formulation in a device capable of generating an aerosol (preferably, an aerosol canister equipped with a valve, and more preferably, a metered dose valve); and actuating the device to form an aerosol of discrete particles that are sufficiently stable to avoid aggregation and film formation under conditions of use (e.g., upon inhalation, upon topical application to a wound, etc.).

Medicinal Salts

It has also been observed that certain biocompatible polymers, such as, for example, low molecular weight poly-$\alpha$-hydroxycarboxylic acids (PHAs), can form salts with many drugs. Such low molecular weight biodegradable polymers, in their salt form with a drug, can provide sustained release of the drug, aid solubilization of the drug, and chemically stabilize the drug, without requiring the presence of additional release controlling matrix materials. Thus, another embodiment of the invention is a medicinal salt of a drug and a low molecular weight biodegradable polymer. The salt comprises: an ionic drug comprising at least one ammonium, sulfonate, or carboxylate group per molecule (preferably, ammonium group); and a biodegradable polymeric counterion comprising at least one ammonium, sulfonate, or carboxylate group (preferably, carboxylate group) and at least one chain of at least three units of the formula $-[O-R^1-C(O)]-$ wherein each $R^1$ is an independently selected organic moiety that links the oxygen atom to the carbonyl group. Preferably, the hydroxyl end of the non-branched chain is esterified. The salt can be used to advantage in various medicinal formulations, whether they be solid, semi-solid, or liquid formulations. Preferred formulations include medicinal aerosol formulations suitable for oral and/or nasal inhalation, such as MDIs.

Such use of a biocompatible low molecular weight polymeric counterion in a medicinal salt of a drug can in many cases provide advantages over the use of a polymeric matrix in a nonionic form. For example, the presence of a biocompatible polymer and the formation of such salts can provide significant improvement in chemical stability over the same formulation without a salt-forming biocompatible polymer.

It can thus be seen from the above that the present invention provides methods, compounds, and medicinal formulations that represent a dramatic advance in providing for enhanced solubilization and chemical stabilization of a drug, as well as providing sustained release of drugs. This is particularly important in the field of aerosol drug delivery, such as for inhalation. The biocompatible polymers described above, particularly the biodegradable polyesters and polyhydroxycarboxylic acids, can be used either as a drug containing matrix or counterion in solid, semi-solid, or liquid formulations. Additional aspects and specific features of the invention will also be apparent by way of the following detailed description and nonlimiting examples of the invention.

DETAILED DESCRIPTION

The present invention provides medicinal formulations containing a drug and a biocompatible polymer. They can be solids, semi-solids, or liquids. Preferred formulations are delivered by oral and/or nasal inhalation, although formulations can also be made for delivery via, for example, topical spray-on administration (e.g., buccal, transdermal). Additionally, compositions (e.g., those made with low polydispersity and/or medicinal salt biocompatible polymers) capable of forming stable preformed solid objects, such as dry powders, microspheres, rods, pins, etc., can be made for delivery by injection, implantation or other suitable methods, as well as oral and/or nasal inhalation.

As discussed below, the medicinal formulations may be made with a variety of drugs, biocompatible polymers, propellants, cosolvents, and other ingredients. Among the benefits provided by the invention, the biocompatible polymer may have enhanced physical and biodegradation properties due to low polydispersity, function as a solubilizing and/or chemical stabilizing aid, provide sustained release, and/or act as a counterion to form a medicinal salt.

Drugs

Medicinal formulations according to the present invention contain a drug either dispersed or dissolved in the formulation in a therapeutically effective amount (i.e., an amount suitable for the desired condition, route, and mode of administration). As used herein, the term "drug," includes its equivalents, "bioactive agent," and "medicament" and is intended to have its broadest meaning as including substances intended for use in the diagnosis, cure, mitigation, treatment or prevention of disease, or to affect the structure or function of the body. The drugs can be neutral or ionic. Preferably, they are suitable for oral and/or nasal inhalation. Delivery to the respiratory tract and/or lung, in order to effect bronchodilation and to treat conditions such as asthma and chronic obstructive pulmonary disease, is preferably by oral inhalation. Alternatively, to treat conditions such as rhinitis or allergic rhinitis, delivery is preferably by nasal inhalation.

Suitable drugs include, for example, antiallergics, analgesics, bronchodilators, antihistamines, antiviral agents, antitussives, anginal preparations, antibiotics, antiinflammatories, immunomodulators, 5-lipoxygenase inhibitors, leukotriene antagonists, phospholipase $A_2$ inhibitors, phosphodiesterase IV inhibitors, peptides, proteins, steroids, and vaccine preparations. A group of preferred drugs include adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-$\alpha$, $\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea and pharmaceutically acceptable salts and solvates thereof, and mixtures thereof Particularly preferred drugs include beclomethasone dipropionate, butixocort propionate, pirbuterol, 4-amino-$\alpha$,$\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof.

For oral and/or nasal inhalation, formulations where the drug is in solution and chemically stable are generally preferred; however, if suspensions are used, preferably the drug is micronized (i.e., in the form of particles having a diameter on the order of micrometers). More preferably, a therapeutically effective fraction of the drug (typically, about 90% or more) is in the form of particles having a diameter of less than about 10 micrometers, and most preferably, less than about 5 micrometers. These particle sizes also apply for the formulations (drug and biocompatible polymer) used in dry powder inhalers. This ensures that the drug can be inhaled into the respiratory tract and/or lungs. It will be recognized that such limitations do not necessarily exist for nasal inhalation.

Preferably, medicinal formulations according to the present invention include a drug in an amount and in a form such that the drug can be administered as an aerosol. More preferably, the drug is present in an amount such that the drug can produce its desired therapeutic effect with one dose from a conventional aerosol canister with a conventional valve, such as a metered dose valve. As used herein, an "amount" of the drug can be referred to in terms of quantity or concentration. A therapeutically effective amount of a drug can vary according to a variety of factors, such as the potency of the particular drug, the route of administration of the formulation, the mode of administration of the formulation, and the mechanical system used to administer the formulation. A therapeutically effective amount of a particular drug can be selected by those of ordinary skill in the art with consideration of such factors. Generally, a therapeutically effective amount will be from about 0.02 parts to about 2 parts by weight based on 100 parts of the medicinal formulation.

Biocompatible Polymers

The preferred biocompatible polymers are condensation-type homopolymers or block or random copolymers. Examples of such polymers can be derived from a hydroxyacid, a mercapto acid, an amino acid, or combinations thereof, such as disclosed in U.S. Pat. No. 5,569,450 (Duan et al.). Other examples of such polymers can be derived from the condensation of a diol with a diacid, such as disclosed in international publication no. WO 94/21228. Preferably, the repeating structural units contain amide units, ester units, or mixtures thereof.

One class of preferred condensation polymers includes at least one chain of at least three units of the formula —[X—$R^1$—C(O)]— (Formula I) wherein: each $R^1$ is an independently selected organic group (which can be linear, branched, or cyclic) that links the X group to the carbonyl group; and each X is independently oxygen, sulfur, or catenary nitrogen. Preferably X is oxygen. In particularly preferred embodiments, at least 50% of said units include oxygen as X. Another class of preferred condensation polymers include at least one chain of at least three units of the formula —[C(O)—$R^2$—C(O)—O—$R^3$—O]— (Formula II) wherein: each $R^2$ is an independently selected organic group (which can be linear, branched, or cyclic) that links the carbonyl groups and each $R^3$ is an independently selected organic group (which can be linear, branched, or cyclic) that links the oxy groups.

In Formulas I and II above, preferably, each $R^1$, $R^2$, and $R^3$ is a straight chain, branched chain, or cyclic organic group (preferably, an alkylene or alkenylene group) containing 1–6 carbon atoms (preferably, 2–6 carbon atoms). Each $R^1$, $R^2$, and $R^3$ can also contain heteroatomic functional groups such as carbonyl groups, oxygen atoms, thiol groups, or fully substituted catenary nitrogen atoms, wherein the nitrogen substituents are free of nucleophilic or hydrogen-donor hydrogen bonding functional groups. $R^1$ preferably contains about 1–4 catenary atoms. Each $R^1$, $R^2$, and $R^3$ can also be an arylene group (e.g., 1,4-phenylene) or an arylene group substituted by functional groups such as lower alkyl groups, lower alkoxy groups, and halogens (preferably, by functional groups that do not contain hydrogen atoms capable of hydrogen bonding, such as lower alkyl or alkoxy groups). As used herein, the term "lower" when used in connection with alkyl, alkenyl, alkoxy, alkenylene, alkylene groups, etc., refers to such groups having 1–4 carbon atoms. Each $R^1$, $R^2$, and/or $R^3$ can also be a combination of such arylene, alkenylene, and alkylene groups, such as 1,4-xylylene.

The chain(s) comprising the units of Formulas I or II can be linear, branched, or cyclic. Such polymers (i.e., those containing chains of units of Formulas I or II) can also optionally include one or more ionic groups, a group that contains one or more hydrogen atoms capable of hydrogen bonding, or a group containing no hydrogen atoms capable of hydrogen bonding.

For the compounds containing at least one chain comprising units of Formula I, the chain(s) comprise units derived from a precursor hydroxyacid, a precursor amino acid, a precursor mercapto acid, or combinations thereof, such as those disclosed in U.S. Pat. No. 5,569,450 (Duan et al.). For the compounds containing at least one chain comprising units of Formula II, the chain(s) comprise units derived from a precursor diacid and a precursor diol. The chains can be homopolymer chains (i.e., those derived from a single such diacid and diol) or copolymer chains (e.g., chains containing randomly distributed units or blocks of units derived from any two or more such diacids or diols). As used herein, a chain "derived from" a particular precursor need not be prepared from the precursor; rather, this terminology is used to designate chains having a structure that could formally be obtained by condensation of the precursor. For example, the units of Formula II are typically referred to as diol/diacid condensate units, although these need not be prepared by the condensation of a diol with a diacid. Rather, this terminology is used to designate chains having a structure that could in principle be obtained by a condensation reaction of a diacid with a diol.

A precursor hydroxyacid can be any hydroxyacid, such as a hydroxy carboxylic acid, or the corresponding lactone or cyclic carbonate, if any. It is preferred that the hydroxyacid be endogenous to the human body. Examples of suitable hydroxycarboxylic acids include straight chain ($C_2$–$C_6$) hydroxyalkyl carboxylic acids such as hydroxyacetic acid, hydroxypropionic acids (e.g., 2- or 3-hydroxypropionic acid), hydroxybutyric acids (e.g., 2-, 3-, or 4-hydroxybutyric acid), hydroxyvaleric acids (e.g., 2-, 3-, 4-, or 5-hydroxyvaleric acid), hydroxycaproic acid (e.g., 2-, 3-, 4-, 5-, or 6-hydroxycaproic acid), branched chain ($C_3$–$C_6$) hydroxyalkyl carboxylic acids (e.g., 2-hydroxydimethylacetic acid), malic acid, malic acid monoesters, and the like. Preferably, the hydroxyacid is an alpha- or a beta-hydroxy carboxylic acid, and more preferably, an alpha-hydroxy carboxylic acid. Suitable lactones include lactides, 1,4-dioxanone (i.e., p-dioxanone), valerolactone, and caprolactone. Suitable cyclic carbonates include trimethylene carbonate.

A precursor amino acid can be any compound having an amino group, preferably, a secondary amino group, at least one carbon atom removed from an acid group such as a carboxylic acid. Exemplary amino acids include secondary amino acids (sometimes referred to as "imino acids") such as sarcosine and proline. As with the hydroxyacids discussed above, it is preferred that the aminocarboxylic acid be endogenous to the human body.

A precursor mercapto acid can be any compound comprising a thiol group and an acid group such as a carboxylic acid group. Exemplary mercapto acids include 2-mercaptopropionic acid, 3-mercaptopropionic acid, and mercaptoacetic acid.

A precursor diacid can be any dicarboxylic acid, e.g., straight chain, branched chain, or cyclic alkylene or alkenylene dicarboxylic acids wherein the alkylene or alkenylene moiety optionally contains heteroatomic functional groups such as carbonyl groups, oxygen atoms, thiol groups, or catenary nitrogen (preferably, fully substituted). Examples of such dicarboxylic acids include oxalic acid, malonic acid, succinic acid, pentane-, hexane-, and heptanedioic acids, and cis- or trans-1,2-cyclohexanedicarboxylic acid. Other precursor diacids include aromatic diacids. Examples of such aromatic diacids include phthalic acid, 1,4-benzenedicarboxylic acid, isophthalic acid, 2,3-furandicarboxylic acid, 1,2-benzenediacetic acid, and the like. Preferred diacids are oxalic and diglycolic acids. The anhydrides corresponding to a dicarboxylic acid are also suitable. Examples of such anhydrides include succinic anhydride, diglycolic anhydride, and the like.

A precursor diol can be any dihydridic alcohol. Suitable precursor diols include straight chain, branched chain, or cyclic alkylene or alkenylene diols optionally containing heteroatomic functional groups such as carbonyl groups, oxygen atoms, thiol groups, or catenary nitrogen (preferably, fully substituted). Examples of such diols include ethylene or propylene glycol, 1,4-butanediol, 1,6-hexanediol, and the like. Other precursor diols include polyoxyalkylene diols. Examples of such diols include polyethylene glycol, polypropylene glycol, and block copolymers comprising polyoxyethylene units and polyoxypropylene units.

Particularly preferred embodiments include polymers wherein the chain comprises units derived from a precursor hydroxyacid (preferably, an alpha- or a beta-hydroxyacid, and more preferably, an alpha-hydroxyacid). More preferably, the chain comprises units derived from a precursor selected from the group consisting of glycolic acid, trimethylene carbonate, alpha- or beta-hydroxybutyric acid, p-dioxanone, and lactic acid. Of these, lactic acid is particularly preferred, whether in the D isomeric form, the L isomeric form, or a mixture of both isomers. Of these, the L form is the most preferred, though in certain applications, the DL form has some advantages due to its amorphous nature and enhanced solubility in, for example, hydrofluorocarbon propellants such as HFC 134a and 227.

One skilled in the art can select units for inclusion in the chains of the biocompatible polymers with consideration of factors, such as mode of administration, ease of metabolism, solubility or dispersibility, crystallinity, structural homogeneity, molecular weight, other components to be used in the medicinal formulations, etc.

Preferred biocompatible polymers as described herein contain at least one chain of units of Formula I. In certain embodiments, the compound can include two or more chains arranged, for example, in connection with divalent and polyvalent capping groups or by inclusion of monomers which cause branching.

A chain can be capped at one end or both ends by a monovalent, divalent, or polyvalent organic moiety (each valence of the capping group being independently bonded to a chain) that does not contain hydrogen atoms capable of hydrogen bonding. The chain can also be capped at one end or both ends by a monovalent, divalent, or polyvalent group, either an ionic group or a group that does contain hydrogen atoms capable of hydrogen bonding. Such groups need not necessarily terminate the compound; rather, they can bridge chains. Examples of groups not containing hydrogen atoms capable of hydrogen bonding include organocarbonyl groups such as acetyl and alkoxy groups such as ethoxy. Examples of ionic groups include quaternary ammonium groups, sulfonate salts, carboxylate salts, and the like. Examples of groups capable of hydrogen bonding include hydrogen when bonded to a heteroatom terminus of a chain, as well as acid functional groups, amides, carbamates, and groups such as amino, hydroxyl, thiol, aminoalkyl, alkylamino, hydroxyalkyl, hydroxyalkylamino, sugar residues, and the like. Such end groups are well known and can be readily selected by those skilled in the art, and are disclosed, for example, in U.S. Pat. No. 5,569,450 and international publication no. WO 94/21228.

The choice of end groups (i.e., capping groups) may modify the performance of the polymer, either in the formulation or biologically. It is preferred for regulatory and biological reasons to minimize the complexity of the biocompatible polymer. However, for physical and chemical reasons it may be preferable to modify the biocompatible polymer with respect to increased stability, propellant solubility (e.g., in hydrofluorocarbons), water affinity/solubility, interaction with the drug, etc. Such parameters frequently influence drug release rates. Preferred biocompatible polymers as described herein contain one chain capped on the hydroxy end with an organocarbonyl group, and more preferably, with an acetyl group. Acylation can significantly enhance stability and reduce the hydrophilicity and water solubility of the biocompatible polymers. Additionally, preferred biocompatible polymers as described herein contain one chain capped on the carbonyl end with a hydroxyl group or with an alkoxy group, such as an ethoxy group. Esterification can enhance biocompatibility and reduce the hydrophilicity and water solubility of the polymers.

Preferably, biocompatible polymers described herein are also biodegradable. As used herein, a "biocompatible" polymer is one that does not generally cause significant adverse reactions (e.g., toxic or antigenic responses) in the body, whether it degrades within the body, remains for extended periods of time, or is excreted whole. A "biodegradable" polymer is one that relatively easily degrades under biological conditions. Typically, biodegradation occurs initially by way of hydrolytic degradation (i.e., hydrolysis of the polymers into smaller molecules).

Biocompatible polymers described herein can have a wide variety of molecular weights. Typically, they should have a number-average molecular weight of no greater than about 5000 (e.g., where n is about 70) because polymers having a number-average molecular weight much higher than this generally are not readily biodegradable. Depending on the particular embodiment and purpose(s) of the biocompatible polymer used therein, the polymers described herein will preferably have a number-average molecular weight of at least about 350, and more preferably, at least about 500, and most preferably greater than about 600. Put in another way, the biocompatible polymers will usually have a preferred chain length of at least 5, and more preferably at least 8 units.

For most embodiments of the polymers containing chain (s) comprising units of Formulas I or II, the chain length (i.e., the average number of monomer units in the chain, often referred to as "n") is defined by no greater than about 70 of said units, preferably, by no greater than about 25 of said units, more preferably, by no greater than about 16 of said units, and most preferably, by no greater than about 11 of said units. Also, the chain length is defined by at least about 3 of said units, and preferably, by at least about 5 of said units. In some embodiments, it is preferable that the compound be substantially free of water soluble polymers so that, for example, the polymer does not quickly dissolve upon delivery to the body tissue, such as the lung, but rather degrades over a desired time period. Generally, the polymers having less than 8 repeat units tend to be water soluble, while polymers having 8 or more repeat units tend to be relatively insoluble, although the precise chain length of course varies with the nature of the repeat units and the nature of the chain end units.

These various preferred molecular weights and chain lengths are by necessity only general guidelines since there are many factors, as will be understood by those skilled in the art, such as the particular polymer type, end-cap groups, and the presence and type of other ingredients (propellants, excipients, etc.), which can greatly affect the choice of molecular weight used.

It is well known that polymers contain a distribution of chain lengths. A particularly preferred embodiment of the present invention has a narrow range of chain lengths, thereby providing a biocompatible polymer having a relatively narrow molecular weight distribution, i.e., low polydispersity. However, in certain embodiments a broad molecular weight distribution may be desired. One skilled in the art will recognize which distribution is preferred for a given application based on the degree of solubility, bulk physical characteristics, biological compatibility and degradation, formulation processability, and performance factors (e.g., solubilizing ability, drug release rate control, shelf life, dose reproducibility, etc.) of the compound.

For certain embodiments of the present invention, suitable biocompatible polymers preferably have a relatively narrow molecular weight distribution. Generally, for such embodiments, the polydispersity (i.e., the ratio of weight-average to number-average molecular weight) is less than about 1.8, preferably less than about 1.6. This is particularly true for certain sustained release formulations utilizing higher molecular weight polymers. Preferably, the polydispersity is less than about 1.4, more preferably less than about 1.3 and, most preferably less than about 1.15. This is particularly true where improved physical characteristics of the composition in solid form are desired or for enhanced solubility in, for example, an aerosol propellant. In contrast, the polydispersity of conventionally made poly-L-lactic acid having a number-average molecular weight of about 1000 or more generally ranges from about 1.6 to 3 with a typical polydispersity greater than 2.2. This is significant because in certain applications a relatively narrow molecular weight distribution provides a material that has an optimized rate of biodegradation. In certain applications this results in an appropriate rate of drug release and improved shelf-life and handling characteristics in its bulk form.

Although it may be preferred to use polymers (described below) having a relatively narrow molecular weight range, it is not required according to all aspects of the invention. For example, when poly-L-lactic acids of normal polydispersity are used in a formulation for pulmonary delivery, it is preferred that the number-average molecular weight of the polymer be no greater than about 800. Otherwise, depending upon the frequency of administration, the higher molecular weight component present can accumulate in the lung. When narrow molecular weight range poly-L-lactic acids (i.e., those having a polydispersity of less than about 1.15) are used, however, the preferred number-average molecular weight is preferably no greater than about 1300, and more preferably, for most inhalation applications, no greater than about 1000. One skilled in the art will recognize that these parameters will vary with each monomer used. For example, when poly-DL-lactic acids of normal polydispersity are used in a formulation for pulmonary delivery, it is preferred that the number-average molecular weight of the polymer be no greater than about 1800, and more preferably no greater than about 1200. Otherwise, depending upon the frequency of administration, the higher molecular weight component present can accumulate in the lung. When narrow molecular weight range poly-DL-lactic acids (i.e., those having a polydispersity of less than about 1.15) are used, however, the preferred number-average molecular weight is preferably no greater than about 2000, and more preferably, for most applications, no greater than about 1600. In general, it is desirable to use the lowest molecular weight biocompatible polymer that still provides adequate incorporation of the drug into the polymer matrix upon delivery, along with the desired release rates.

As already noted, it is generally preferred that the biocompatible polymers of the present invention are biodegradable. Preferably, such polymers are sufficiently biodegradable such that they have a biological half-life (e.g., in the lung) of less than about 10 days, more preferably, less than about 4 days, even more preferably, less than about 2 days, and most preferably, less than about 1 day. For certain embodiments of the present invention, biocompatible polymers are sufficiently biodegradable in use such that medicinal formulations containing them have a biological half-life of less than about 7 days. Preferably, for embodiments, such as those formulations capable of being inhaled, the biological half-life is less than about 2 days (more preferably, less than about 1 day, even more preferably, less than about 12 hours, and most preferably, less than about 6 hours). As used herein, "biological half-life" is the time required for half the mass of the material to disappear from the original site in vivo.

For certain embodiments of the present invention, the biocompatible polymer has a glass transition temperature (Tg) such that the glass transition temperature of a composition that includes the biocompatible polymer, a drug, and additional optional excipients, is above about 23° C. That is, the Tg of the biocompatible (preferably, biodegradable) compound itself may be above or below about 23° C., as long as that of a mixture of the biocompatible polymer with a drug and optional excipients is above about 23° C. Preferably, and advantageously, this Tg can be reached without the aid of additional excipients in the polymer. Typically, such preferred biocompatible polymers are polymers having a polydispersity of less than about 1.15. Surprisingly, it has been discovered that when the biocompatible polymer is combined with a drug, the Tg of the mixture is typically greater than that of the biocompatible polymer itself, which renders a broader range of polymers in the medicinal formulation to be generally morphologically shelf stable. Generally, the Tg of the biocompatible polymer is such that the Tg of a composition that includes the biocompatible polymer, a drug, and optional excipients, is below about 100°0 C., although it is often much less than this.

Thus, certain preferred biocompatible polymers described herein can be combined with a drug to form a rapidly degrading, morphologically shelf stable polymeric matrix, which can be in the form of a dispersion, or dry powder, for example. Such biocompatible polymers are preferably homo-polymers having linear chains of units derived from an alpha-hydroxy carboxylic acid, such as L-lactic acid, and preferably have a number-average molecular weight of greater than 700 and no greater than about 1500, and more preferably no greater than about 1200, and a polydispersity of less than about 1.15. Put another way, the preferred average chain length (n) of the polymer is about 10–16 units.

The optimal amount of the biocompatible polymer depends on its nature, what role it serves within the formulation, and the nature of the drug with which it is used. A practical upper limit in aerosol formulations is based on the solubility of the polymer. The solubility levels of individual biocompatible polymers are a function of the molecular weight and polydispersity of the polymer, as well as the chemical nature of the repeating units and endgroups. In general, the solubilities of the polyhydroxycarboxylic acids (for a given molecular weight) increase as their tendency toward crystallization decreases. For example, poly-DL-lactic acid is generally more soluble than poly-L-lactic acid.

For aerosol formulations, the biocompatible polymer is generally present in dissolved form in an amount of from about 0.01 part to about 25 parts by weight based on 100 parts of the medicinal formulation, preferably from about 0.1 part to about 10 parts by weight based on 100 parts of the medicinal formulation, and for some applications preferably from about 1 part to about 5 parts by weight based on 100 parts of the medicinal formulation.

Method to Produce Narrow Distribution Polymers

Polymers according to the present invention having a narrow molecular weight range (e.g., a polydispersity of less than about 1.3, and preferably, less than about 1.15) can be prepared using a supercritical fluid fractionation method. The solvent power of supercritical fluids can be tuned by changing the supercritical fluid density (via pressure/temperature), hence either the quantity of solute or maximum molecular weight solubilized can be selected by adjusting the pressure/temperature conditions. This adjustability provides a substantial benefit over normal liquid solvent fractionation.

Thus, the present invention provides a method of producing a polymeric compound having, for example, a number-average molecular weight of no greater than about 1500, and a significantly reduced polydispersity (e.g., less than about 1.3 and, preferably, less than about 1.15). The method comprises sequentially exposing the polymeric compounds to a flow of supercritical fluid under different pressure/temperature conditions. The particular type of supercritical fluid apparatus used is not limited as long as the biocompatible polymer has good contact with supercritical fluid. Thus, for example, the fractionation may be enacted using a single vessel with a increasing pressure profile techniques or alternatively, one may use a series of pressure vessels with a decreasing pressure profile techniques. The supercritical fluid is preferably selected from the group consisting of carbon dioxide, 1,1,1,2-tetrafluoroethane (also referred to as propellant 134a, HFC-134a, or HFA-134a), 1,1,1,2,3,3,3-heptafluoropropane (also referred to as propellant 227, HFC-227, or HFA-227), nitrogen dioxide, ethylene, ethane, trifluoromethane, xenon, or blends of the above. While a wide variety of supercritical fluids are useful in the present invention, it is preferred that they be nonreactive with the biocompatible polymer being fractionated and nontoxic. More preferably, the supercritical fluid is carbon dioxide.

This method of polymer fractionation using supercritical fluid provides significant advantages. Besides the unexpected technical superiority, it also provides advantages over conventional solvent fractionation which has high costs, environmental disadvantages, and raises health concerns due to residual contamination.

Drug Solubilization and Chemical Stabilization

It has been found that in certain aerosol formulations the drug is more soluble when a biocompatible polymer as described herein is present than when the biocompatible polymer is not present. Of course, this depends on a number of factors, such as the type and amount of drug as well as the type and amount of biocompatible polymer. In some instances, solubility is enhanced by a relatively high concentration (e.g. greater than 1% by weight) of a relatively low molecular weight biocompatible polymer (e.g., number average MW less than about 350). Alternatively, a low to moderate concentration (e.g., 0.01 to 1% by weight) of a higher molecular weight (e.g., number average MW greater than about 600) biocompatible polymer can increase the solubility of some drugs. Also, it has been found that in certain formulations, dissolved drug is chemically more stable (and thus has a longer shelf life) with a biocompatible polymer as described herein than when in a formulation without such biocompatible polymer. For example, aerosol solution formulations of drugs containing amine groups are known to often have a relatively short shelf life; however, when combined with a suitable biocompatible polymer (e.g., one that is capable of forming a salt with the amine-containing drug dissolved in the formulation) the shelf life may be improved.

It should also be pointed out that the same biocompatible polymer may aid in solubilizing a given drug if present in a relatively large amount (e.g., greater than about 1 part by weight based on 100 parts of the medicinal formulation), and yet function as a dispersing aid if present in smaller amounts (e.g., less than about 0.1 part by weight based on 100 parts of the medicinal formulation). In general, longer chain polymers having a molecular weight of at least about 600 that strongly interact with the drug are good solubilizers at lower weight percentages of the formulation, while shorter chain polymers having a molecular weight of less than about 350 typically function as solubilizers at higher weight percentages of the formulation. However, these are general descriptions only, as the specific parameters vary with each drug/polymer combination.

For aerosol formulations wherein the biocompatible polymer is acting as a solubilizing and/or chemical stabilizing aid, the number-average molecular weight is preferably no greater than about 1500, more preferably, no greater than about 1200, and most preferably, no greater than about 800.

Sustained Release Aerosol Formulations

One preferred embodiment of the present invention is a sustained release medicinal aerosol formulation including a propellant, a drug, and a soluble biocompatible polymer. Such medicinal formulations are preferably suitable for nasal and/or oral inhalation. By this it is meant, among other things, that when delivered from a metered dose inhaler they form particles of a size appropriate for nasal and/or oral inhalation and do not typically form films. These particles are formed spontaneously as the formulation exits the aerosol valve and the propellant evaporates. Hence, although the biocompatible polymers described herein may be used to make preformed sustained release microparticles (e.g., microspheres) by conventional means, the present invention also provides a method for automatically generating sustained release microparticles from an aerosol spontaneously upon valve actuation, without requiring any preformed microparticles. That is, the method includes the steps of: preparing a sustained release medicinal aerosol formulation by combining components comprising a propellant, and a sufficient amount of a biocompatible polymer substantially completely soluble in the medicinal formulation to provide for sustained drug release, and a drug as a micronized suspension or substantially completely dissolved in the medicinal formulation in a therapeutically effective amount; placing the medicinal formulation in a device capable of generating an aerosol (preferably, an aerosol canister equipped with a valve, and more preferably, an aerosol canister equipped with a metered dose valve); and actuating the device to form an aerosol comprising particles that are sufficiently stable to avoid aggregation and film formation under conditions of use.

A sustained release formulation is one that releases the drug over an extended period of time (e.g., as short as about 60 minutes or as long as several hours and even several days or months), rather than substantially instantaneously upon administration. Typically, for a polymer matrix of a particular size, the sustained release characteristics are determined by the nature of the biocompatible polymer and of the drug. Also, it is determined by the relative amount of biocompatible polymer to drug.

A sustained release medicinal formulation includes a biocompatible polymer in an amount such that the period of therapeutic activity of the drug is increased relative to the activity of the same formulation with respect to the propellant and drug but without the biocompatible polymer. Preferably, this increase is by a factor of at least about 1.5. Alternatively, for certain embodiments, it is preferred that the sustained release medicinal formulation includes a biocompatible polymer in an amount such that the period of therapeutic activity of the drug is extended by the presence of the biocompatible polymer by at least about 30 minutes, and more preferably, by at least about 2 hours, and most preferably, by at least about 6 hours. When used in aerosol formulations, it will be understood by one of skill in the art that a direct comparison of the same formulation without the biocompatible polymer may not be possible due to formulation difficulties when the biocompatible polymer is absent. Thus, a conventional dispersant and/or cosolvent may need to be added to the medicinal formulation to provide an inhalable formulation for comparison of the period of time during which the drug is present at levels needed to obtain a desired biological response. However, such formulation changes may prevent a perfectly parallel comparison of the release rates.

The amount of biocompatible polymer (total mass relative to drug) that will be sufficient to provide sustained release over a desired period of time depends, among other things, on the form of the drug. In the case of aerosol formulations containing the drug in micronized particle form (i.e., dispersed in the formulation), the amount of biocompatible polymer (preferably, biodegradable polymer) that will generally be sufficient is at least enough to provide a substantially complete layer or coating around the micronized particles after exiting the aerosol valve. This amount is typically considerably greater than the amount that is used when such polymers are used solely as dispersing aids. It is typically at least about a 1:1 molar ratio of biocompatible polymer to drug. Preferably, the molar ratio of biocompatible polymer to drug is greater than about 4:1 on a molar basis. Alternatively, on a weight basis there will be typically at least about a 1:1 ratio of biocompatible polymer to drug. Preferably, on a weight basis there will typically be at least about a 4:1 ratio, and more preferably at least about an 8:1 ratio of biocompatible polymer to drug.

In the case of aerosol formulations containing the drug in solution (i.e., substantially completely dissolved in the formulation), the amount of biocompatible polymer (preferably, biodegradable polymer) sufficient to provide sustained release varies considerably. In general, at least about a 1:1 molar ratio of biocompatible polymer to drug is desirable, although lesser amounts may be used to provide partial sustained release (e.g., bi-phasic release, etc.) and/or as a solubilization aid for the drug. Alternatively, on a weight to weight basis, the ratio of polymer to drug is generally between about 1:1 and about 100:1. Preferably, the amount of biocompatible polymer for sustained release of a drug in dissolved form is typically between about 2:1 to about 30:1 weight ratio of biocompatible polymer to drug, and more preferably, about 4:1 to about 15:1 on a weight basis. Again, however, the desired amount can depend on many factors, including the desired release times, nature of the drug or agents involved, the nature and number of biocompatible polymers used, as well as the average molecular weight(s) of the biocompatible polymer(s) and their polydispersities. In general, larger weight ratios of polymer to drug will lead to slower drug release rates. Those skilled in the art will be readily able, based on the teachings herein, to incorporate and assess the various factors to suit a particular application of the invention.

For sustained release aerosol formulations, the number-average molecular weight is generally no greater than about 5000, typically no greater than about 1800, preferably, no greater than about 1200, and more preferably, no greater than about 800. Also, it is generally preferred that the molecular weight is greater than about 600. Put another way, the average chain length (n) of the polymer is preferably less than about 25 units, more preferably between about 5–20 units, and most preferably between about 8–14 units. Also, it is generally preferred to use the lowest polydispersity which still provides the desired release rate.

Medicinal Drug-Polymer Salts

Certain biodegradable polymers described herein can be combined with a drug to form a medicinal salt. Thus, medicinal salts are provided that include an ionic drug that includes at least one carboxylate group, ammonium group, or sulfonate group per molecule and a biodegradable polymer counterion that includes at least one ammonium or conjugate base derived from a carboxylic or sulfonic acid group (preferably, carboxylic acid group) and a chain of at least three units of the formula —[O—$R^1$—C(O)]— discussed above. Preferably, the ionic drug includes at least one ammonium group and the biodegradable polymer counterion includes at least one carboxylate group. Ammonium group refers to any amine-derived ionic moiety (e.g., groups derived from primary, secondary, tertiary, and heterocyclic amines by protonation, as well as quaternary ammonium).

The molecular weights, polydispersity, and other characteristics of the biocompatible polymers previously described herein also generally apply here, where the biodegradable polymer acts as a counterion. The polydispersity and the molecular weight of the biodegradable polymer counterions are important variables in determining the profile of drug availability over time. This is particularly true if mixtures or blends of biodegradable polymer counterions having different molecular weight distributions are used, thereby forming bimodal, trimodal, etc., formulations. Preferably, the biodegradable polymers that form the medicinal salt are linear chains and have a number-average molecular weight of no greater than about 1500 (more preferably, about 500 to about 1000). The preferred polydispersity and molecular weight will of course vary with the desired drug release profile.

Most preferably, the biodegradable polymer used in forming the medicinal salt is primarily derived from alpha-hydroxy carboxylic acids containing only one carboxylate group. Additionally the polymer preferably is esterified on the hydroxy end with a low molecular weight acyl group. The salt-forming biodegradable polymer is preferably present in at least a one-to-one molar ratio relative to the salt-forming drug, and more preferably in at least one equivalent relative to the salt-forming groups of the drug. Under certain circumstances it may be advantageous to include an excess of the biodegradable polymer. Additionally, it is within the scope of the present invention to include a lesser amount of the biodegradable polymer, particularly wherein the unbound drug has different pharmacokinetic behavior than the salt form.

The medicinal salts may be substantially soluble or substantially insoluble in a propellant used in a aerosol medicinal formulation. They may also be used in non-aerosol formulations. Also, a medicinal salt can be dispersed within a matrix comprising a second biocompatible polymer (preferably, a biodegradable compound), which preferably will have a higher molecular weight than that of the biocompatible polymer forming the salt with the drug. This dispersion can be either homogeneous, or it can be heterogeneous such that discrete domains of the salt are formed within the matrix. Preferably, the second biocompatible polymer forming the matrix is biodegradable, of the formula —[X—$R^1$—C(O)]— and has a number-average molecular weight greater than about 1800. However, formulations having the drug and the salt-forming biodegradable polymer with no additional biocompatible polymer matrix compounds are generally preferred.

Propellants

Preferred medicinal formulations according to the present invention include a propellant. Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. Preferably, the propellant includes a chlorofluorocarbon, a hydrochlorofluorocarbon, a hydrofluorocarbon, or mixtures thereof. More preferably, a hydrofluorocarbon is used as the propellant. Most preferably, HFC-227 and/or HFC-134a are used as the propellant. The propellant is preferably present in an amount sufficient to propel a plurality of doses of the drug from an aerosol canister, preferably a metered dose inhaler.

Conventional aerosol canisters, such as those of aluminum, glass, stainless steel, or polyethylene terephthalate, can be used to contain the medicinal formulations according to the present invention. Aerosol canisters equipped with conventional valves, preferably, metered dose valves, can be used to deliver the formulations of the invention. The selection of the appropriate valve assembly typically depends on the components in the medicinal formulation.

Cosolvent and Other Additives

Medicinal formulations according to the present invention can include an optional cosolvent or mixtures of cosolvents. The cosolvent can be used in an amount effective to dissolve the drug and/or the biocompatible polymeric compound. Preferably, the cosolvent is used in an amount of about 0.01–25% by weight based on the total weight of the formulation). Nonlimiting examples of suitable cosolvents include ethanol, isopropanol, acetone, ethyl lactate, dimethyl ether, menthol, tetrahydrofuran, and ethyl acetate. Ethanol is a preferred cosolvent, although it is believed that in at least some circumstances ethanol may tend to degrade the polymer and, hence, isopropanol or a less nucleophilic solvent may be preferred.

Other additives (i.e., excipients), such as lubricants, surfactants, and taste masking ingredients, can also be included in medicinal formulations of the present invention.

EXPERIMENTAL EXAMPLES

The following experimental examples are provided to further illustrate various specific and preferred embodiments and techniques of the invention. It should be understood, however, that many variations and modifications may be made while remaining within the scope of the present invention. All parts and percentages are by weight unless otherwise indicated. All materials were used as obtained unless otherwise indicated. Solvents and inorganic reagents were obtained from EM Science, Gibbstown, N.J. Lactic acid and lactides were obtained from Purac America Inc., Lincolnshire, Ill. All other reagents were obtained from Aldrich Chemical Co., Milwaukee, Wis.

In the preparations of biocompatible polymers set forth below, the structure and the average number (n) of repeating units in a chain were determined by $^1$H nuclear magnetic resonance spectroscopy. The number-average molecular weight Mn and the weight-average molecular weight Mw were determined using gel permeation chromatography (GPC) or supercritical fluid chromatography (SFC). The GPC instrument used was a Hewlett-Packard 1090-LUSI equipped with a UV detector set at 254 nm and a refractive index detector (HP 1037A). The column set comprised 500 Angstrom columns from Jordi Associates, Bellingham, Mass. The samples were dissolved in tetrahydrofuran at an approximate concentration of 25 mg solids/10 mL and pressure filtered through a 0.2 micron alpha cellulose filter. An injection size of 150 µL was handled by a Hewlett-Packard 9816 computer with software supplied by Nelson Analytical, Cupertino, Calif. Molecular weight data are based on a calibration with polystyrene standards.

The SFC instrument used was a Dionex/Lee 602(Salt Lake City, Utah) equipped with a flame ionization detector at 425° C. The column was a 10 meter, 25% cyanopropyl, 50 micron ID, 0.25 micron film from Dionex-Lee Scientific Div., Salt Lake City, Utah. The samples were derivatized with diazomethane, dissolved in chloroform at an approximate concentration of 20 mg solids/1 mL and pressure filtered through a 0.2 micron polyvinylidenefluoride (PVDF) filter. Direct injection of 200 µL took 0.1 second. Conditions were isothermal (110° C.) using super critical $CO_2$ as the carrier gas with a continuous ramp of 0.71 MPa/minute from 8.1 MPa to 42 MPa. Molecular weight data are calculated from the area of each individual polymer. Individual polymers were identified by comparison of retention times versus well-characterized nominally monodisperse PLA samples.

Thermal properties (glass transition, melting, and degradation points; Tg, Tm, $T_{deg}$) were determined utilizing a modulated differential scanning calorimeter (DSC) TA Instruments, New Castle, Del. A linear heating rate of 5° C./minute was applied, with a perturbation amplitude of ±1° C. every 60 seconds. The samples were examined by applying a cyclic heat-cool-heat profile ranging from −144.5° C. to 244.5° C. The glass transition temperatures (Tg) reported were taken at the midpoint in the change in heat capacity over the step transition, and were evaluated using the reversing signal curve. Mass median aerodynamic diameters of the aerosol were determined using a Quartz crystal microbalance (QCM) cascade impactor (model PE2AS/202/207; California Measurements Inc., Sierra Madre, Calif.) as described in Pharmaceutical Research, 12, S-181, 1995.

Examples 1–21

Preparation of Biocompatible Polymers

Example 1

L-lactide (200 grams; 1.39 moles) and water (150 mL; Millipore, Bedford, Mass.) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 10.5 hours the reaction was cooled to 80° C. and 600 mL of chloroform was added with stirring. The organic layer was extracted twice with 200 mL of water in a separatory funnel and dried with $MgSO_4$. The mixture was filtered through a "d" fritted glass funnel and the solvent distilled from the polymer by rotary evaporation. The polymer was transferred to a clean 1000 mL 3-neck flask equipped as described above and 200 mL acetic anhydride was added. The solution was stirred at 80° C. overnight under a slow nitrogen purge. After 12 or more hours the remaining acetic anhydride and acetic acid were removed under vacuum. After the acetic acid/acetic anhydride distillation was complete, 180 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (600 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=8.8, Mn=860, Mw=1151. The product was then distilled at 0.4 mm Hg at 156° C. (3×) on a falling film molecular still to remove certain low MW polymers resulting in acetyl-poly (L-lactic acid) with n=9.0, Mn=933, Mw=1233 (by GPC).

Example 2

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 6 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 230 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Ethyl acetate (700 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.4. The product was then distilled at 0.4 mm Hg at 110° C. (1×), 156° C. (3×) on a falling film molecular still to remove certain low MW polymers resulting in acetyl-poly (L-lactic acid) with n=8.6, Mn=685, Mw=859 (by SFC).

Example 3

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (14 mm Hg) and the temperature was raised to 140° C. to distill off water. After 10 hours the temperature was raised to 160° C. After a total of 13 hours the reaction was cooled to 80° C. and acetic anhydride (220 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 230 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (700 mL) was added and the resulting solution was extracted twice with millipore water (300 mL) in a separatory funnel and then dried twice with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=9.52. The polymer was dissolved in ethyl acetate at 16.5% solids and isopropyl alcohol was added until the solution began to become cloudy. The solution was sealed and allowed to sit overnight, during which time some of the polymers precipitated. The solution was filtered through a "c" fritted glass funnel using $Na_2SO_4$ as a fritter aid. The filtration was repeated using an "f" flitted glass funnel. The product was then distilled at 0.4 mm Hg at 110° C. (4×) on a falling film molecular still to remove certain low MW polymers resulting in acetyl-poly (L-lactic acid) with n=9.9, Mn=666, Mw=882 (by SFC).

Example 4

L-lactide (200 grams; 1.38 moles) and water (200 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 6 hours the reaction was cooled to 80° C. and acetic anhydride (200 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 180 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (600 mL) was added and the resulting solution was extracted twice with millipore water (200 mL) in a separatory funnel and then dried with $MgSO_4$. The mixture was filtered through a "d" flitted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.6. The product was then distilled at 0.4 mm Hg at 190° C. (3×) on a falling film molecular still to remove certain low MW polymers resulting in acetyl-poly (L-lactic acid) with n=9.2, Mn=529, Mw=707 (by SFC).

Example 5

DL-lactic acid (300 grams; 2.83 moles) was placed in a 1 L 3-neck flask equipped with a mechanical stirrer, distillation head, and a thermometer. The flask was then placed under vacuum (7 mm Hg) and the temperature was raised to 140° C. to distill off water. After 8 hours the reaction was cooled to 80° C. to provide poly (DL-lactic acid) with n=6.4. The product was then placed under vacuum (7 mm Hg) and the temperature was again raised to 140° C. for 2 hours to provide poly (DL-lactic acid) with n=11.4, Mn=925, Mw=1670 (by GPC).

Example 6

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 8 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 270 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (750 mL) was added and the resulting solution was extracted three times with millipore water (250 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.4. The product was then distilled at 0.4 mm Hg at 110° C. (2×) on a falling film molecular still to remove polymers with two or less repeat units resulting in acetyl-poly (L-lactic acid) with n=8.1, Mn=592, Mw=751 (by SFC).

Example 7

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 8 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 270 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (750 mL) was added and the resulting solution was extracted three times with millipore water (250 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.5. The product was then distilled at 0.4 mm Hg at 110° C. (1×), 156° C. (3×), and 212° C. on a falling film molecular still to remove certain low MW polymers resulting in acetyl-poly (L-lactic acid) with n=13, Mn=958, Mw=1077 (by SFC).

Example 8

Five lots of acetyl-poly (L-lactic acid), prepared as in example 7, were combined and distilled at 0.4 mm Hg at 212° C. (2×) on a falling film molecular still to obtain an acetyl-poly (L-lactic acid) with n=11.5. As described in example 22, 8.52 g of this polymer was then placed in a sample extraction cartridge connected to a Dense Gas Management (DGM) System and sequentially fractionated. Supercritical fluid $CO_2$ flow was initiated at 27.5 Bar at 60° C. and 2.76 g of acetyl-poly (L-lactic acid), was removed and discarded. A second fraction was collected at 37.5 Bar at 60 ° C. to obtain 2.96 g of acetyl-poly (L-lactic acid) with n=12.8, Mn=982, Mw=1087 (by SFC).

Example 9

L-lactic acid (258 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 16 hours the reaction was cooled to 80° C. and acetic anhydride (200 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 300 mL of tetrahydrofuran/water (85/15; volume/volume) was added with stirring and the flask temperature was allowed to drop to 40° C. After 30 minutes the reaction mixture was transferred to a round bottom flask and the tetrahydrofuran was removed under vacuum on a rotary evaporator. Chloroform (300 mL) was added and the resulting solution was extracted with water then dried with $MgSO_4$. The mixture was filtered through a "d" fritted glass funnel and the solution was diluted with hexane until a second phase formed. The chloroform layer was collected and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=14, Mn=1118, Mw=2100 (by GPC).

Example 10

L-lactide (199 grams; 1.38 moles) and water (200 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 6 hours the reaction was cooled to 80° C. and acetic anhydride (200 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 180 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (600 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.4. The product was then distilled at 0.4 mm Hg at 110° C. (1×), 156° C. (3×) and 212° C. (2×) on a falling film molecular still to remove certain low MW polymers resulting in acetyl-poly (L-lactic acid) with n=9.07, Mn=829, Mw=1038 (by GPC).

Example 11

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 6 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 230 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Ethyl acetate (700 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.4. The product was then distilled at 0.4 mm Hg at 110° C. (2×), 156° C. (3×) on a falling film molecular still to remove certain low MW polymers resulting in acetyl-poly (L-lactic acid) with n=10, Mn=715, Mw=865 (by SFC).

Example 12

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 4 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 180 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Ethyl acetate (1 L) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=6.4. The product was then distilled at 0.4 mm Hg at 110° C. (1×), 156° C. (3×) on a falling film molecular still to remove certain low MW polymers resulting in acetyl-poly (L-lactic acid) with n=6.64, Mn=524, Mw=576 (by SFC).

Example 13

Six lots of acetyl-poly (L-lactic acid) with average n values ranging from 5 to 9 were combined and final traces of solvents were removed under high vacuum (0.4 mm Hg)

on a Kugelrohr apparatus at 90° C. The product was then distilled at 0.4 mm Hg at 156° C. (2×) on a falling film molecular still to remove polymers resulting in acetyl-poly (L-lactic acid) with n=8.54, Mn=762, Mw=1032 (by GPC).

Example 14

DL-Lactic acid (150 grams of a nominally 85% solution in water; 1.42 moles) and glycolic acid (46.1 grams; 0.61 moles) were combined and heated (120–140° C.) under aspirator vacuum with stirring for 23 hours. Acetic anhydride (310 grams) was added and the resulting mixture was heated with stirring for about 150 minutes to remove acetic acid. Water (146 mL) was added. The volatiles were removed by distillation under aspirator vacuum followed by rotary evaporation. The crude product was dried under high vacuum over the weekend. The crude product was then extracted with chloroform. The chloroform extract was washed 4 times with dilute hydrochloric acid then evaporated. The residue was dried under high vacuum overnight to provide 130 grams of acetyl-poly(DL-lactic-co-glycolic acid). Based on proton nuclear magnetic resonance spectroscopy, the product had a total chain length of n=12 with an average of 8.7 lactic acid units and 3.4 glycolic acid units randomly distributed therein and wherein Mn=578 and Mw=867 (by GPC).

Example 15

L-Lactic acid (200 grams of a nominally 85% solution in water; 1.89 moles) and toluene (1200 mL) were combined and heated for 24 hours to azeotropically remove water. Acetic anhydride (289 grams; 2.84 moles) was added and the reaction was heated for an additional 2 hours. Water (50 mL) was added and the reaction mixture was heated for an additional hour during which time 300 mL of solvent were removed. The volatiles were removed by distillation under aspirator vacuum followed by rotary evaporation. The crude product was dissolved in chloroform (80 mL). The chloroform solution was washed with dilute hydrochloric acid then evaporated to provide acetyl-poly(L-lactic acid). A portion of this material was chlorinated as follows: Oxalyl chloride (32.7 mL; 0.375 moles) was added dropwise to a cooled (0° C.) solution containing acetyl-poly(L-lactic acid) (40 grams) in 1,2-dichloroethane (400 mL). The reaction mixture was stirred at 0° C. for an hour after the addition was completed. The reaction mixture was heated slowly to 45° C. and stirred at this temperature overnight during which time most of the 1,2-dichloroethane evaporated. Oxalyl chloride (10.9 mL) and 1,2-dichloroethane (250 mL) were added and the reaction mixture was heated at 50° C. for 1 hour. The reaction mixture was heated under aspirator vacuum to remove the volatiles. The residue was dried on a rotary evaporator and then under high vacuum to provide 33.7 g of acetyl-poly(L-lactoyl) chloride wherein n=4.7. The acetyl-poly(L-lactoyl) chloride (33.7 grams, 0.081 mole) was dissolved in chloroform (200 mL). Glycine (15.8 grams; 0.211 mole) and sodium hydroxide (8.42 grams; 0.211 mole) were dissolved in water (45 mL). The two solutions were combined and stirred at ambient temperature for 4 hours. Hydrochloric acid (25 mL) was added to adjust the pH to 2; then the reaction mixture was diluted with chloroform (80 mL). The phases were separated and the organic phase was evaporated to provide a crude product. The crude product was partitioned between chloroform and water. The chloroform layer was evaporated to provide material that by proton nuclear magnetic resonance spectroscopy was a 70:30 mixture of acetyl-poly(L-lactoyl) N-glycine and acetyl-poly(L-lactic acid) with n=4.0, Mn=491 and Mw=565 (by GPC).

Example 16

DL-2-Hydroxycaproic acid (1.00 grams, 0.0076 mole) was placed in a mini reaction flask (5 mL) equipped with a distillation head and magnetic spin vane. The flask was heated at 110° C. for 24 hours under low vacuum (aspirator). Acetic anhydride (1 gram; 0.0098 mole) was added to the polymer, followed by heating at 110° C. for 18 hours. Excess acetic anhydride and acetic acid were distilled off under low vacuum. Tetrahydrofuran/water (1 mL of 85/15; volume/volume) was added with stirring and heating at 60° C. for 0.5 hour. The bulk of the solvent was removed by vacuum distillation on a rotary evaporator. The resulting crude product was dissolved in chloroform (10 mL). The chloroform solution was washed twice with Millipore water (5 mL) and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 120° C. to provide acetyl-poly(DL-hydroxycaproic acid) with n=7.4, Mn=830, and Mw=1214 (by GPC).

Example 17

DL-2-Hydroxycaproic acid (1.00 gram, 0.0076 mole), and L-lactic acid (4.5 grams of a nominally 85% solution in water; 0.043 mole) were placed in a reaction flask equipped with a distillation head and mechanical stirrer. The flask was heated at 110° C. for 6 hours under low vacuum (aspirator) while water was removed. The temperature was then raised to 140° C. for 6 hours. Acetic anhydride (5.16 grams; 0.0506 moles) was added to the polymer, followed by heating at 80° C. for 14 hours. Excess acetic anhydride and acetic acid were distilled off under low vacuum. Tetrahydrofuran/water (15 mL of 85/15; volume/volume) was added with stirring and heating at 60° C. for 0.5 hour. The bulk of the solvent was removed by vacuum distillation on a rotary evaporator. The resulting crude product was dissolved in chloroform (20 mL). The chloroform solution was washed twice with millipore water (5 mL) and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 120° C. to provide acetyl-poly(DL-2-hydroxycaproic-co-L-lactic acid) with n=7.5 for lactic acid and 1.4 for hydroxycaproic acid, Mn=763, and Mw=1044 (by GPC).

Example 18

L-Lactide (8.72 grams; 0.061 mole), p-dioxanone (1.34 grams, 0.013 mole) and water (10 mL; Millipore) were placed in a 50 mL 3-neck flask equipped with a mechanical stirrer, distillation head, and a thermometer. The reaction mixture was warmed to 80° C. and stirred under nitrogen overnight. The flask was then placed under vacuum (aspirator, 7 mm Hg) and the temperature was raised to 110° C. to distill off water. After 1 hour, 200 $\mu$l of tin octanoate (0.33 M in toluene) was added and the reaction proceeded for 16 hours. The flask was cooled to 80° C. and 10 mL of acetic anhydride was added. The solution was stirred at 80° C. overnight under a slow nitrogen purge. After 8 hours the remaining acetic anhydride and acetic acid were removed under vacuum. After the acetic acid and acetic anhydride distillation was complete, 25 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (50 mL) was added and the resulting solution was extracted twice with 20 mL of millipore water in a separatory funnel and then dried with $MgSO_4$. The mixture was filtered through a "d" fritted glass funnel and the solvent distilled from the polymer by rotary evaporation. Final traces of solvents and monomer were removed under high vacuum (0.4 mm Hg) on a Kugelrohr apparatus at 90° C. to yield acetyl-poly (dioxanone-co-L-lactic acid) with dioxanone n=0.6, lactic acid n=7.5.

Example 19

Several lots of acetyl-poly (L-lactic acid) were distilled at 0.4 mm Hg at 110° C. (1×), 156° C. (3×), and 212° C. (3×) on a falling film molecular still obtain a distillate of low MW polymers, primarily with a range of n=2–6, and an average n=4.14. This distillate was then distilled at 0.4 mm Hg at 110° C. (3×) on a falling film molecular still resulting in acetyl-poly (L-lactic acid) with n=4.96, primarily with a range of n=3–6, Mn=383, Mw=406 (by SFC).

Example 20

L-lactide (300 grams; 2.08 moles) and water (300 mL; Millipore) were placed in a 1 L 3-neck flask equipped with a mechanical stirrer, distillation head, and a thermometer. The reaction was warmed to 80° C. and stirred under nitrogen overnight. The flask was then placed under vacuum (7 mm Hg) and the temperature was raised to 140° C. to distill off water. After 6 hours the reaction was cooled to 80° C. and acetic anhydride (300 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 230 mL of tetrahydrofuran/water (85/15; volume/volume) was added with stirring and the flask temperature was allowed to drop to 60° C. After 15 minutes the reaction mixture was transferred to a round bottom flask and the tetrahydrofuran was removed under vacuum on a rotary evaporator. Chloroform (700 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactic acid) with n=5.8. The product was then distilled at 0.4 mm Hg at 110° C. (2×), 156° C. (3×) on a falling film molecular still to remove certain low MW polymers resulting in acetyl-poly (L-lactic acid) with n=6.5, Mn 708, Mw=803 (by GPC).

Example 21

L-lactide (200 grams; 1.39 moles) and ethyl lactate (0.82 gram, 0.79 ml) were placed in a 250 mL single-neck flask equipped with a stir bar and, reflux head The reaction was warmed to 150° C. and stirred under nitrogen overnight. The flask was then transferred to a Kugelrohr distillation unit, and placed under vacuum (7 mm Hg) at 140° C. with rocking. After 6 hours the reaction was cooled to 80° C. and acetic anhydride (15 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, the polymer was dissolved in 100 mL of acetonitrile and extracted with hexane (2×30 ml). The acetonitrile layer was transferred to a round bottom flask and the acetonitrile was removed under vacuum on a rotary evaporator. Chloroform (700 mL) was added and the resulting solution was extracted twice with millipore water (200 mL) in a separatory funnel and then dried with $MgSO_4$. The mixture was filtered through a "d" fritted glass funnel and the solvent distilled from the polymer by rotary evaporation. Final traces of solvents were removed under high vacuum (0.4 mm Hg) on a Kugelrohr apparatus at 90° C. to provide acetyl-poly (L-lactoyl)-O-hydroxyethane with n=21.8, Mn=1530, Mw=2400 (by GPC).

Examples 22–23

Supercritical Fluid Fractionation of Polymers

Polymer fractionation was carried out using a Dense Gas Management (DGM) System, commercially available from Marc Sims SFE Inc. Berkeley, Calif. using supercritical fluid (SCF) techniques known to those skilled in the art. In a typical fractionation according to the present invention, PLA (8 grams) and clean 2 mm glass beads (20 g) were transferred into an 100 mL sample cartridge, then inserted into a 300 mL Dense Gas Management System extraction vessel. The sample cartridge was equipped with a 30 micron metal frits on both ends. Supercritical fluid $CO_2$ (Anhydrous instrument grade 99.99% from Oxygen Services Co., St. Paul, Minn.) flow was initiated at the temperature and pressure described in Tables 1 and 2 to remove each fraction in a glass U-tube. As each fraction was collected, the U-tube was changed and the pressure was increased (optionally the temperature could also be changed) and supercritical fluid $CO_2$ flow was continued. Upon completion of the fractionation, the supercritical fluid $CO_2$ was vented down to atmospheric pressure and the residual fraction was collected from the sample cartridge by dissolution into methylene chloride or ethyl acetate. These examples demonstrate the general capability of supercritical fluids to fractionate both derivatized (e.g., esterified) and underivatized polymers as well as both amorphous and semi-crystalline polymers.

Example 22

Supercritical Fluid Fractionation of the Polymer from Example 4

The capability of supercritical fluids to fractionate derivatized (e.g., acetylated) polyhydroxy carboxylic acids (PHAs) and remove selective distributions of PHAs is demonstrated in Table 1. In this example, supercritical fluid fractionation of the derivatized semi-crystalline L isomer from Example 4 resulted in 7 cuts, each with unique Mn's and polydispersity distributions (P) more narrow than the starting material.

TABLE 1

Supercritical Fluid Fractionation of the Polymer from Example 4

| Fraction | Pressure, MPa | Temp., ° C. | $CO_2$, L | Mn | Mw | P |
|---|---|---|---|---|---|---|
| Cmpd of Ex. 4 | — | — | — | 529 | 707 | 1.34 |
| 1 | 11.0 | 50 | 130 | 295 | 346 | 1.17 |
| 2 | 15.0 | 50 | 332 | 323 | 358 | 1.11 |
| 3 | 20.0 | 50 | 224 | 443 | 485 | 1.09 |
| 4 | 25.0 | 50 | 250 | 613 | 668 | 1.09 |

TABLE 1-continued

Supercritical Fluid Fractionation of the Polymer from Example 4

| Fraction | Pressure, MPa | Temp., °C. | $CO_2$, L | Mn | Mw | P |
|---|---|---|---|---|---|---|
| 5 | 30.0 | 50 | 197 | 823 | 913 | 1.11 |
| 6 | 35.0 | 50 | 692 | 1134 | 1230 | 1.09 |
| 7(residual) | — | — | — | 1284 | 1417 | 1.1 |

Example 23

Supercritical Fluid Fractionation of the Polymer from Example 5

The capability of supercritical fluids to fractionate underivatized (e.g., containing a hydroxyl endgroup) polyhydroxy carboxylic acids (PHAs) and remove selective distributions of PHAs is demonstrated in Table 2. In this example, supercritical fluid fractionation of the amorphous non-derivatized DL isomeric polymer from Example 5 resulted in 10 cuts, each with unique Mn's and distributions more narrow than the starting material.

TABLE 2

Supercritical Fluid Fractionation of the Polymer from Example 5

| Fraction | Pressure, MPa | Temp., °C. | Grams $CO_2$ | Mn | Mw | P |
|---|---|---|---|---|---|---|
| Cmpd of Ex. 5 | — | — | — | 925 | 1670 | 1.81 |
| 1 | 20.0 | 60 | 668 | 323 | 482 | 1.49 |
| 2 | 22.5 | 60 | 510 | 409 | 581 | 1.42 |
| 3 | 25.0 | 60 | 713 | 445 | 647 | 1.44 |
| 4 | 27.5 | 60 | 641 | 754 | 947 | 1.26 |
| 5 | 30.0 | 60 | 824 | 982 | 1180 | 1.20 |
| 6 | 32.5 | 60 | 831 | 1210 | 1450 | 1.19 |
| 7 | 35.0 | 60 | 770 | 1750 | 1950 | 1.11 |
| 8 | 37.5 | 60 | 1000 | 1950 | 2140 | 1.10 |
| 9 | 40.0 | 60 | 700 | 2400 | 2590 | 1.08 |
| 10(residual) | — | — | — | 3540 | 4080 | 1.15 |

Examples 24–29

Properties of Biocompatible Polymers

Example 24

Solubility Properties

Attempts to solubilize a variety of polylactic acids and polylactic/glycolic copolymers in HFC134a and HFC227 demonstrated that polyhydroxycarboxylic acids of the type previously utilized in pulmonary drug delivery, such as those described by E. Poyner, J. Cont. Rel., 35, 41–48 (1995) (PLA2000) and L. Masinde, Int. J. Pharmaceutics, 100, 123–131 (1993) (PLA100,000), were insoluble in the HFCs. Poly-L-lactic acid obtained from Polysciences Inc., Warrington, Pa., [L-PLA 100,000, 50,000 and 2,000 (catalog nos. 18402, 06529, and 18580)] were insoluble in both HFC134a and HFC227 at 0.1% weight/weight after 10 minutes of sonication at ambient conditions. Likewise, polylactic/glycolic acids copolymers [DL-PLAGA 5,000: 9/1 and 50,000: 8/2 (catalog nos. 19076 and 19077)] were insoluble at 0.1%. After one day, DL-PLAGA 5,000: 9/1 exhibited partial solubility. Poly-DL-Lactic acid [DL-PLA 20,000 (catalog no. 16585)] was soluble at 0.1% but not fully soluble at 1%.

Polymers, as exemplified by the compounds of Examples 1–21, were typically fully soluble in HFC 227 at 1% by weight with levels commonly approaching 3%. The solubility levels of individual polymeric hydroxycarboxylic acids were a function of the polymers molecular weight and polydispersity, as well as the chemical nature of the repeating units and endgroups. In general, the solubilities of the polyhydroxycarboxylic acids were increased if their tendency towards crystallization was reduced. For example, DL-lactic acid was substantially more soluble than L-lactic acid, which was more soluble than polyglycolic acid for a given molecular weight and polydispersity. Likewise, the lower molecular weight polymers were more soluble than their higher molecular weight counterparts. And for a specified molecular weight, the polymer with a lower polydispersity typically exhibited a greater degree of solubility.

Example 25

PLA Degradation

Comparative studies between relatively low molecular weight polylactic acids (<1800; some with low MW polydispersity distributions) and polylactic acid with a nominal molecular weight of 2000 were conducted by subcutaneous implantation of cylinders (10×1 mm) of PLA held separately in sealed polypropylene woven mesh envelopes (2×1 cm) into New Zealand rabbits. Polypropylene mesh envelopes were used to facilitate the handling of the PLA compound of Example 6 and PLA2000 [Polysciences Inc., PA., (catalog no. 18580)] and to ease removal of the implants at the desired times. The explants were analyzed by NMR and quantified by supercritical fluid $CO_2$ chromatography (SFC). The compounds used are described in Table 3. The compound of Example 6 and PLA2000 are composed of unaltered distributions from their molecular weights resulting from synthesis (i.e., the distributions are substantially unchanged from those obtained by their synthesis). PLA2000 appears to be the lowest molecular weight polylactic acid which is presently commercially available. The compounds of Examples 7 and 8 are examples of low polydispersity distributions of PLAs, with unique properties and value. The compound of Example 7 was obtained by molecular distillation removal of very low (n=1 to 7) molecular weight polymers from a "normal" distribution. The compound of Example 8 was obtained by supercritical fluid fractionation to remove both low and high molecular weight fractions from the original distribution.

TABLE 3

SFC Analysis of Polymers used in Biodegradation Studies

| Polymer | Description | Mn | P |
|---|---|---|---|
| Example 6 | Unaltered polymer | 592 | 1.26 |
| Example 7 | Novel polymer by distillation | 958 | 1.12 |
| Example 8 | Novel polymer by SCF fractionation | 982 | 1.11 |
| PLA2000 | Commercial low MW polymer | 2150 | 2.54 |

Table 4 compares the degradation of narrow distribution polymers (polymers of Examples 7 and 8) during the first 4 days of implantation, to normal distribution polymers of Example 6 and PLA2000. The polymers of Examples 6, 7, and 8 rapidly degrade, with more than 85% of the polymer absorbed within 24 hours of implantation. PLA2000 had not begun to degraded at 4 days. Indeed, degradation of PLA2000 was not observed even after 10 days. This obser vation was in agreement with the literature which indicated a half-life ranging from 63 to 191 days for PLA2000.

TABLE 4

Weight Percent Remaining after Implantation of Bulk PLAs

| Compound Time, days | Example 6 Weight % | Example 7 Weight % | Example 8 Weight % | PLA2000 Weight % |
|---|---|---|---|---|
| 0 | 100 | 100 | 1000 | 100 |
| 1 | 10.4 | 10.4 | 12.3 | 95.1 |
| 4 | 11.1 | 11.1 | 8.9 | 105.5 |

The low molecular weight polymeric lactic acids are clearly rapidly absorbed in-vivo, making them highly desirable for applications requiring rapid clearance. The degradation of polylactic acids is likely to be faster in the preferred inhalation applications than that observed in the above study. Degradation times typically correlate with implant dimensions and the implant study was conducted with relatively large cylindrical matrices which would be expected to degrade slower than the microparticles used in certain preferred inhalation applications of the invention. Furthermore, the lung is a more robust environment, being rich in esterases and other defensive mechanisms, compared with a subcutaneous implant site. Additionally, in this implant study, significant amounts of unidentified (non-PLA) components of biological origin were incorporated into the explant by the fourth day. This biological component partially interfered with the analysis of the implants and caused an overestimate of the amount of PLA remaining. Hence, the observed degradation can be considered the slowest probable degradation rate.

Supporting this hypothesis, two metabolism studies (via intraperitoneal injection and aerosol inhalation in the rat utilizing $^{14}C$ radio-labeled PLA of identical chemical composition and similar molecular weight distribution to the polymer of Example 6 in Table 3 exhibited an initial half-life of 2 hours with >80% being eliminated within 24 hours. In the first study, two male Charles River CD rats were dosed with 10 mg (0.24 $\mu$Ci/mg) of $^{14}C$ radio-labeled PLA by intraperitoneal injection of a DMSO solution (0.2 mls). Complete urinary, fecal and $CO_2$ collections were made until 4 days post dose. Tissues were collected at the time of sacrifice. In the second study, the same compound was administered to 5 rats by a 30 minute nose-only inhalation exposure. The doses were delivered from an HFC 227 metered dose inhaler containing 0.9% PLA (51.5 $\mu$Ci total) into a cylindrical chamber (34 cm h×13.4 cm dia.) equipped with individual rat holding tubes. The entire contents of the vial were delivered to the rats. the rats were transferred to glass metabolism cages and complete urinary, fecal and $CO_2$ collections were made until 3 days post dose. Tissues were collected at the time of sacrifice. In both studies the overall disposition of $^{14}C$ radio-labeled PLA resembled that of endogenous lactic acid as reported in the literature.

These results clearly indicate low molecular weight hydroxycarboxylic acid polymers (PHAs) have the highly desirable trait of rapid biodegradation which is needed for the safe frequent inhalation of PHAs. These results also clearly indicate that hydroxycarboxylic acid polymers of narrow molecular weight distributions (compounds of Examples 7 and 8) have been obtained which retain the rapid absorption of low molecular weight conventional PLAs. The next example demonstrates the improved physical properties of these relatively narrow molecular weight distributions.

Example 26

Glass Transition Temperatures (Tg)

The Tg's of polymeric compounds of Examples 6, 7, 8 and PLA2000 were determined by modulated DSC. The compound of Example 6 (Mn=592) had a Tg well below room temperature (4.2° C.). Compounds of Example 7 (Mn=958), Example 8 (Mn=982), and PLA2000 (Mn=2150) had Tg's above room temperature (23° C., 25° C., and 44° C., respectively).

These data and that in Table 4 demonstrate that by modifying the naturally occurring distribution of the molecular weights (i.e., polydispersity) of these polymeric compounds, relatively narrow molecular weight distributions can be obtained that retain the rapid bioabsorption/biodegradation of the compound of Example 6 while exhibiting Tg's above room temperature. Thus, materials with Tg's greater than room temperature were obtained by removing low molecular weight polymers, which results in an increase in the Mn. For polymers of the same chemical composition, Tg's are known to vary with the Mn of the polymer as described by the Flory-Fox equation. The biodegradation times were shortened by controlling the weight percent of the slowly degrading high molecular weight polymers, especially polymers having a tendency towards forming a crystalline phase. Polymers were fractionated into useful distributions by supercritical fluid techniques as shown in Examples 22 and 23. Useful distributions were also obtained by removing low molecular weight polymers by the method of molecular distillation discussed in U.S. Pat. No. 5,569,450 (WO 94/21229) and exemplified by the compound of Example 7.

The resulting combination of properties—rapid biodegradation with good physical properties—is extremely useful for many drug delivery systems and is not believed to have been previously demonstrated using PHA polymers or the like. For example, one preferred application of such formulations is in dry powder inhalers.

Example 27

Drugs in Polymer Matrices

It is common for smaller molecules (e.g., plasticizers) to be added to polymers to reduce and broaden the Tg, thereby improving the polymer's processing or flexibility. Hence, the possibility existed that some drugs might behave as plasticizers when added to the polymers, which would reduce the range of PHAs useful for solid preformed matrices, for example, as used in dry powder inhalers. Consequently, the effect of a variety of drugs on the compound of Example 7 was examined. Surprisingly, the data in Table 5 demonstrates that the drugs actually raised the Tg of the matrix, allowing a broader range of PHAs to be used due to the improved handling characteristics of the PHA-drug mixture. Thus, comparing the Tg of the PHA matrix material (the compound of Example 7) to the Tg of the polymer composition with drug present demonstrated an increase of the Tg of the polymer/drug mixture relative to the Tg of the original matrix material. It is believed that this ability of the drug to improve the material properties of the matrix material has not been reported previously. It will also be recognized that other biologically acceptable molecules (e.g., excipients) which are not the active agent, may be added to improve the matrix material's properties.

TABLE 5

Effect of Drug on the Tg of PLAs

| Compound/Mixture | PLA/Drug Mole/Mole Ratio | Tg |
|---|---|---|
| PLA of Example 7 | x | 23 |
| Chlorhexidine base | 0 | 38.5 |
| Chlorhexidine base + PLA of Ex. 7 | 1 | 37.5 |
| Chlorhexidine base + PLA of Ex. 7 | 8 | 33.6 |
| Lidocaine | 0 | none detected |
| Lidocaine + PLA of Ex. 7 | 1 | 36.7 |
| Lidocaine + PLA of Ex. 7 | 4 | 26 |
| Lidocaine HCl | 0 | 30.7 |
| Lidocaine HCl + PLA of Ex. 7 | 1 | 33.2 |
| Lidocaine HCl + PLA of Ex. 7 | 4 | 25.1 |
| Tetracycline | 0 | 50.5 |
| Tetracycline + PLA of Ex. 7 | 1 | 36.1 |
| Tetracycline + PLA of Ex. 7 | 6 | 29.9 |
| Tetracycline HCl | 0 | 50.5 |
| Tetracycline HCl + PLA of Ex. 7 | 1 | 28.2 |
| Tetracycline HCl + PLA of Ex. 7 | 4 | 30.5 |
| Tetracycline HCl + PLA of Ex. 7 | 6 | 29.9 |
| Triamcinolone acetonide | 0 | none detected |
| Triamcinolone acetonide + PLA of Ex. 7 | 1 | 25.7 |
| Triamcinolone acetonide + PLA of Ex. 7 | 4 | 24.6 |
| Triamcinolone acetonide + PLA of Ex. 7 | 6 | 26.4 |
| Albuterol | 0 | 48.9 |
| Albuterol + PLA of Ex. 7 | 1 | 15.29 |
| Albuterol + PLA of Ex. 7 | 4 | 24.3 |
| Albuterol sulfate (2/1) | 0 | 49 |
| Albuterol sulfate + PLA of Ex. 7 | 1 | 24.6 |
| Albuterol sulfate + PLA of Ex. 7 | 5 | 25.9 |
| Kanamycin sulfate | 0 | 49 |
| Kanamycin sulfate + PLA of Ex. 7 | 1 | 27.6 |
| Kanamycin sulfate + PLA of Ex. 7 | 3 | 24.5 |
| Kanamycin sulfate + PLA of Ex. 7 | 7 | 22.9 |

Example 28

Biodegradable Polymer/Drug Salts

Changes in drug melting points (Tm) as determined on a modulated DSC provided evidence for salt formation between the drug and the PLA of Example 7 as shown in Table 6. The salts were prepared by mixing suitable solutions (e.g., acetone, chloroform, methanol) of the drug and PLA in the desired ratio, followed by evaporation and extensive drying under high vacuum to remove all traces of solvent. As later examples demonstrate, these novel salt complexes alter the bioavailability of the drug and can provide a new manner to control drug release. Among the PHAs, alpha-PHAs are preferred because they exhibit very low pKa's (>3.5) and are rapidly biodegraded. Bioavailability frequently correlates with the water solubility of the drug-complex. The water solubility of the PHAs is dependent on the molecular weight and the nature of the end groups. For example, non-esterified polylactic acid is water-soluble up to a molecular weight of 522 (7 repeat units) with some authors reporting up to 882 (12 repeat units) as being water soluble. Acetylated polylactic acids are not water soluble beyond 276 (3 repeat units).

Thus, for example, if an acetylated polylactic acid of molecular weight greater than 564 is used it is unlikely to provide a water soluble complex until the chain has been hydrolyzed at one ester bond. The molecular weight of the acylated polymer necessary to provide an insoluble salt is dependent both on the nature of the drug and the end-group used. It will be recognized that the characteristics (MW, distribution, chemical nature, endgroups, etc.) of the polymer counter-ion will be important to the ultimate pharmacokinetics of the drug. Furthermore, the ability to provide tailored kinetics (e.g., zero-order, pulsed) should be possible by blending different polymers. Thus, the biodegradability of the counterion provides a new method to alter the pharmacokinetics of the drug. Additionally, the increased thermal stability of the salt complex over the free base drug exemplifies the utility of such polymers as stabilizers. In the preferred application (MDIs) the ability of PHAs to form stabilizing salts with amine-containing drugs is especially valuable when the salts are soluble in the propellant formulation (such as in HFCs 134a and 227).

TABLE 6

Thermal Properties

| Compound | PLA/Drug Molar Ratio | Tm, °C. | Degradation Temperature, °C. |
|---|---|---|---|
| PLA of Example 7 | — | none (amorphous) | >225 |
| Chlorhexidine base | 0 | 132 | >225 |
| Chlorhexidine base + PLA of Ex. 7 | 1 | 192 | >225 |
| Lidocaine | 0 | 68 | 159 |
| Lidocaine + PLA of Ex. 7 | 1 | 91 | >225 |
| Tetracycline | 0 | 158 | 179 |
| Tetracycline + PLA of Ex. 7 | 1 | >225 | >225 |
| Tetracycline + PLA of Ex. 7 | 6 | >225 | >225 |

Example 29

Polymers as Solubilizing Aids

The insolubility of many drugs, along with the typically poor shelf life (long term chemical stability) of those drugs which may form solutions, has presented a general problem to formulators. The stabilizing effect of PHAs is presented in Table 6. The general utility of PHAs to aid in the preparation of propellant solution formulations has been demonstrated, for example, by the ability of polylactic acids to increase the solubility of drugs in the propellants HFC 134a and 227. The solubilizing effect of the polymers is demonstrated in Table 7. It also displays the effect of cosolvents and polymer structure on the polymer's ability to function as a solubilizer for a given drug. When cosolvents were present, synergistic increases in solubility were sometimes observed. The utility of PHAs to provide stable solution formulations provides a significant advance in the inhalation drug delivery art.

TABLE 7

Solubilization of Drugs in Propellant by Weight-% of PLA

| Drug (%), HFC | Cmpnd | 0% PLA | 0.10% PLA | 1% PLA | 2.70% PLA |
|---|---|---|---|---|---|
| Albuterol base (0.01), 134a | Ex. 2 | insol | sol at 0.03% | sol | |
| Albuterol base (0.05), 134a | Ex. 19 | insol | * | sol | * |
| Albuterol sulfate (0.01), 227 | Ex. 2 | insol | insol | insol | * |
| Albuterol sulfate (0.01), 227 | Ex. 19 | insol | insol | insol | * |
| Budesonide (0.02), 227 + 2% EtOH | Ex. 19 | insol | * | sol | * |
| Budesonide (0.015), 227 | Ex. 19 | insol | insol | insol | insol |
| Butixocort propionate (0.08), 227 | Ex. 2 | insol | * | insol | sol |
| Butixocort propionate (0.08), 227 + 0.5% EtOH | Ex. 2 | insol | * | * | sol |
| Butixocort propionate (0.08), 134a | Ex. 2 | insol | * | * | sol |
| Chlorhexidine (0.05), 134a | Ex. 2 | insol | * | sol | * |
| Chlorhexidine (0.03), 227 | Ex. 2 | insol | * | sol | sol |
| Chlorhexidine (0.03), 227 | Ex. 19 | insol | * | sol | * |
| Dibekacin (0.008), 134a | Ex. 2 | insol | insol | insol | * |
| Lidocaine (1.0), 134a | Ex. 19 | insol | * | * | sol at 5% |
| Lidocaine (1.0), 227 | Ex. 2 | insol | * | * | sol at 3.4% |
| Pirbuterol Acetate (0.01), 227 | Ex. 2 | insol | * | sol | * |
| Pirbuterol Acetate (0.01), 227 | Ex. 19 | insol | * | sol | * |
| Rifampicin (0.04), 134a | Ex. 19 | insol | insol | sol | sol |

*data not collected

Examples 30–34

Sustained Release Formulations

The PLA formulations shown in Table 8 were prepared and tested for sustained release in vivo. PLAs were used to prepare solution and suspension aerosol formulations using the following general method. The drugs and PLAs were weighed into a 120 mL glass aerosol vial along with the cosolvent if needed. A continuous or metered valve was crimped onto the vial and the vial was pressure filled with propellant, either HFC 134a or HFC 227, to provide a stock solution containing the desired weight-% of PLA and drug. The stock solutions were then used as is or cold-fill transferred to 15 mL vials equipped with metered dose valves using techniques known in the art. The following drugs were used: 4-amino-α,α,2-trimethyl-1H-imidazo[4,5-c]quinoline-1-ethanol ("IMQ") and disclosed in Comparative Example C1 in U.S. Pat. No. 5,266,575; 2,5-diethyl-10-oxo-1,2,4-triazolo[1,5-c]pyrimido[5,4-b][1,4]thiazine ("PD4") and disclosed as Example 148 in U.S. Pat. No. 4,981,850; 1-(1-ethylpropyl)-1-hydroxy-3-phenylurea ("5LO") and disclosed as Compound 42 in International Publication No. WO 96/03983; butixocort propionate ("BTX"); and beclomethasone dipropionate ("BDP").

TABLE 8

| Formula | HFC | Drug; wt-% | PLA Cmpnd; wt-% | Cosolvent; wt-% |
|---|---|---|---|---|
| Example 30 | 227 | IMQ; 0.079 | PLA of Ex. 9; 0.83 | EtOH; 9.3 |
| Example 31 | 227 | BDP; 0.337 | PLA of Ex. 13; 3.37 | EtOH; 8.0 |
| Example 32 | 134a | BTX; 0.32 | PLA of Ex. 1; 3.36 | EtOH; 7.7 |
| Example 33 | 227 | PD4; 0.09 | PLA of Ex. 1; 1.15 | EtOH; 8.3 |
| Example 34 | 227 | 5LO; 0.091 | PLA of Ex. 3; 0.91 | EtOH 13.2 |

Example 30

Sustained Release of IMQ

The formulation of Example 30 in Table 8 and its PLA free analogue were administered to mice by inhalation. Typical inhalation exposure systems were comprised of but not limited to, an aerosol generator, e.g., an MDI, an aerosol expansion space, and a housing device which ensures the animals must inhale the aerosol, e.g., a flow-past inhalation chamber. Typically, the animals were exposed to 20 actuations per minute for 25 minutes of an MDI generated 2 micron average MMAD aerosol. Lung lavage and bleeding of the exposed mice, were performed by standard methods known to those skilled in the art and tumor necrosis factor (TNF) analyses were performed by an ELISA method specific for TNF in the mouse (Genzyme Immunobiologicals, Cambridge, Mass.). TNF is a marker for this drug's activity. Pulmonary therapy application of IMQ prefers drug activity localized in the lung. Therefore, it was desirable to maintain high levels of drug in the lung and minimize systemic drug. However, this formulation and method could also clearly be used to provide long term release of IMQ or analogous compounds for systemic applications. The results are presented in Table 9. The lavage numbers are measurements of TNF levels in the lung while the serum levels measure systemic TNF levels.

TABLE 9

| Time (hours) after dosing | IMQ with Compound of Ex. 9. TNF level (pg/ml) | | IMQ alone TNF level (pg/ml) | |
|---|---|---|---|---|
| | Lavage | Serum | Lavage | Serum |
| 0 | 0 | 0 | 40 | 13 |
| 1 | 0 | 275 | 105 | 6 |
| 2 | 1209 | 202 | 213 | 193 |
| 4 | 218 | 0 | 144 | 577 |
| 72 | 42 | 0 | * | * |

* data not collected

These results show that IMQ alone produced the greatest activity, as seen by TNF production, in the serum rather than the lung lavage. The addition of PLA reversed this result by causing the greatest activity of TNF production in the lung along with the longest duration of activity in the lung. IMQ was used in its free base form and thus formed a biodegradable salt complex with the compound of Example 9. This biodegradable polymer-IMQ salt was soluble in the HFC based propellant system. This example also demonstrated the generation of microspheres for sustained release, and the utility of biodegradable polymeric counterions in drug delivery.

Example 31

Sustained Release of BDP

The formulation of Example 31 in Table 8 and its PLA free analogue were administered to adult dogs by inhalation. Sedated dogs were intubated with a low pressure cuff endotracheal tube (Hi-Lo Jet®, Mallinkrodt, Glen Falls, N.Y.). The side port was fitted with a Delrin® actuator and the MDI was fired through the side port tube, typically 20 times over 10 minutes. Serum samples were collected over time and analyzed for the beclomethasone dipropionate metabolite, specifically free beclomethasone. The results are presented in Table 10.

TABLE 10

| | Beclomethasone in Serum (pg/ml) | |
|---|---|---|
| Time (minutes) after dosing | BDP with Compound of Ex. 13 | BDP |
| −9 | 0 | 0 |
| 3 | 0 | 31 |
| 63 | 46 | 75 |
| 122 | 72 | 68 |
| 183 | 195 | 72 |
| 242 | 238 | 70 |
| 296 | 237 | 80 |
| 357 | 335 | 100 |

These results show that BDP alone produced serum metabolite levels quickly, suggesting low residence time of BDP in the lung. BDP/PLA not only caused a delay in the appearance of metabolite in serum, but also resulted in higher levels over a longer time, showing the BDP/PLA formulation resulted in longer lung residence time. Prior experiments indicated BDP alone typically had reached peak concentrations by 350 minutes after exposure. BDP is a steroid and lacks the ability to form a salt complex with the compound of Example 13. Hence, this example demonstrates the utility of biodegradable polymeric-hydroxycarboxylic acids with hydrophobic drugs in sustained release drug delivery. This biodegradable polymer and non-salt forming steroid were soluble in the HFC-based propellant system and provide another example of the generation of microspheres for sustained release.

Example 32

Sustained Release of Butixocort Propionate

The formulation of Example 32 in Table 8 and its PLA free analogue were delivered into the respiratory track and lungs of adult dogs. Sedated dogs were intubated with a low pressure cuff endotracheal tube (Hi-Lo Jet®, Mallinkrodt, Glen Falls, N.Y.). The side port was fitted with a Delrin® actuator and the MDI was fired through the side port tube. Blood samples were collected from the dogs and the primary metabolite of BTX (JO-1605) was assayed. The results are presented in Table 11.

TABLE 11

| | Metabolite Levels (ng/ml) | |
|---|---|---|
| Time (hrs) after dosing | BTX with the Compound of Ex. 1 | BTX |
| 0.0 | 0.0 | 0.1 |
| 0.5 | 1.9 | 5.3 |
| 1.5 | 2.1 | 2.9 |
| 2.5 | 2.6 | 1.2 |
| 3.5 | 3.7 | 1.1 |
| 4.5 | 3.3 | 0.5 |
| 5.5 | 4.0 | * |
| 6.5 | 3.4 | * |

*data not collected

These results showed after the BTX exposure, the appearance of metabolite (JO-1605) in the blood was rapid, peaked soon, and diminished quickly. The addition of the Compound of Example 1 to BTX caused the presence of JO-1605 to be greatly extended compared to the non-PLA formulation. Thus, PLA formulations exhibited an increased drug residence time in the lungs. BTX is a steroid and lacks the ability to form a salt complex with the polymers. Hence, this example demonstrates the utility of biodegradable polymeric-hydroxycarboxylic acids with hydrophobic drugs in sustained release drug delivery and provides another example of the generation of microsphere particles for sustained release.

Example 33

Sustained Release of PD4

MDI Formulation Example 33 in Table 8 and its PLA free analogue were given to mice by inhalation and the amount of PD4 was determined for lung lavage fluid and serum. Typical inhalation exposure systems were comprised of but not limited to, an aerosol generator, e.g., an MDI, an aerosol expansion space, and a housing device which ensures the animals must inhale the aerosol, e.g., a flow-past inhalation chamber. Typically, 15 mice were continually exposed to a 0.88 micron MMAD aerosol generated from a pressure vessel for 11 minutes. The results are presented in Table 12.

TABLE 12

| Time (minutes) after dosing | PD4 with the Compound of Ex. 1 ($\mu$g) | | PD4 ($\mu$g) | |
|---|---|---|---|---|
| | Lavage | Serum | Lavage | Serum |
| 10 | 0.342 | 2.81 | 0.032 | 3.19 |
| 60 | 0.146 | 2.02 | 0.008 | 7.38 |

These results show that PD4 alone produced small levels of drug in the lung lavage fluid and large proportional amounts in the serum. PD4/PLA produced much greater levels of drug in the lavage fluid and smaller proportional amounts in the serum, especially after 60 minutes past exposure, suggesting that PLA caused longer lung drug residence time. This example demonstrates the utility of sustained release, localized delivery aerosol formations, and salt formation.

Example 34

Sustained Release of 5LO

The formulation of Example 34 in Table 8 and its PLA free analogue were given to male Hartley guinea pigs by inhalation and evaluated by the guinea pig early phase anaphylactic response test. Typical inhalation exposure systems were comprised of an aerosol generator, e.g., an MDI, a 150 ml aerosol expansion chamber, and a trachea cannula. Each guinea pig received 4 actuations containing 32 ug drug/actuation. The guinea pigs were antigen (ovalalbumin) challenged at varied times and pulmonary dynamic compliance was tested using a Buxco pulmonary mechanics analyzer (Buxco Electronics, Sharon Conn.) according to the method of Amdur and Mead (The American Journal of Physiology, Vol. 92, pp. 364–368 (1958)). The results are presented in Table 13.

TABLE 13

| Time (minutes) of challenge after dosing | Percent Inhibition of Bronchoconstriction: 5LO with the compound of Ex. 3 | 5LO |
|---|---|---|
| 15 | * | 67% |
| 30 | * | 48% |
| 60 | 78% | 4% |
| 120 | 58% | * |

* data not collected

These results show that the activity of 5LO as measured by bronchoconstriction inhibition was nearly at background at the 60 minute time point compared to the activity of 5LO/PLA which exhibited activity out to at least 120 minutes. Thus, PLA caused sustained activity of 5LO.

Examples 35–60

In vitro Sustained Release Studies

To minimize the use of animals associated with the in vivo studies a number of in vitro studies were conducted to further exemplify the invention. These studies were based on the release of drug from an PLA-drug impregnated matrix. The matrix was used to facilitate easy handling of the systems and did not affect the release of drug. In a typical example, the drug (exemplified by lidocaine (1.46 mg, 6.24 mM)) and PLA (exemplified by the compound of Example 10) were dissolved in 125 mL of acetone. To 50 mL of this solution, 72 filter paper disks (one inch diameter) were added and allowed to soak for 15 hours. After air drying, the drug/PLA impregnated disks were dried under reduced pressure (0.05 mm Hg) for 2 hours. The disks were the placed in separate 1 ounce vials containing 5 mL of 0.02 M acetate buffer. At the desired test times, an aliquot was removed, acidified with 0.1 M HCl to a pH of 1, and filtered through a 0.2μ PTFE filter (Millipore) and the absorbance read at the desired wavelength (e.g., 264 nm for lidocaine) to determine the amount of drug released. The method used above was used to prepared the specific compositions in Table 14. The data in Table 14 presents the effect that the PHAs had on the release of the selected compounds. Disks impregnated only with drug released the drug within 5 minutes.

TABLE 14

| | | | Mole Ratio | Coating Weight, | Mole % Released at Time (minutes) | | | | | |
|---|---|---|---|---|---|---|---|---|---|---|
| Ex. # | PLA Cmpnd | Drug | PLA/drug | g/disk | 15 min | 45 min | 90 min | 180 min | 360 min | 720 min |
| 35 | PLA of Ex. 7 | Lidocaine | 4 | 0.054 | 39 | 44 | 43 | 51 | 56 | 78 |
| 36 | PLA of Ex. 7 + PLAGA (1:1 ratio) | Lidocaine | 1 | 0.0542 | 26 | 36 | 45 | 70 | 77 | 82 |
| 37 | PLA of Ex. 10 | Chlorhexidine | 4 | 0.0011 | 14 | 23 | 26 | 34 | 35 | * |
| 38 | PLA of Ex. 10 | Albuterol base | 1 | 0.054 | 50 | 54 | 49 | 88 | 94 | 99 |
| 39 | PLA of Ex. 10 | Albuterol base | 10 | 0.005 | 69 | 78 | 87 | 99 | * | * |
| 40 | PLA of Ex. 10 | Tetracycline | 4 | 0.054 | 11 | 26 | 41 | 49 | 53 | 57 |
| 41 | PLA of Ex. 10 | Tetracycline | 10 | 0.003 | 85 | 91 | 95 | * | * | * |

PLAGA is Medisorb 85% DL-lactide-15% glycolide, IV = .76, Mn = 160,000
*data not collected The PHA formulations shown in Table 15 were prepared for use within metered dose inhalers. PHAs were used to prepare solution and suspension aerosol formulations of the invention using the following general method. The active agent and PHAs were weighed into a four ounce (120 mL) glass aerosol vial along with the cosolvent if needed. A continuous valve was crimped onto the vial and the vial was pressure filled with propellant, either HFC 134a or HFC 227, to provide a stock solution containing the desired weight-% of PHA and drug (optionally with a cosolvent). Utilizing glass vials allowed visual evaluation of the formulation. Using standard techniques known in the art, the formulations were chilled with dry ice to allow cold transfer to smaller vials equipped with metered dose valves. The metered dose valves were then actuated and the mass median aerodynamic diameters (MMAD) of the aerosol thus produced were determined using a Quartz crystal microbalance.

TABLE 15

| Example | Drug; weight-% | Cmpnd; Weight-% | HFC | Cosolvent; Weight-% | Result | MMAD, μm |
|---|---|---|---|---|---|---|
| 42 | Budesonide; 0.1 | Ex. 1; 1 | 227 | EtOH; 8 | Solution | 1.88 |
| 43 | Fluticasone; 0.1 | Ex. 1; 1 | 227 | EtOH; 1 | Suspension | 1.60 |
| 44 | Pentamidine Isethionate; 0.1 | Ex. 1; 1 | 227 | EtOH; 8 | Suspension | 2.12 |
| 45 | Cromoglycate $Na_2$; 0.1 | Ex. 1; 1 | 227 | EtOH; 3 | Suspension | 2.39 |
| 46 | Cromoglycate $Na_2$; 0.1 | Ex. 1; 1 | 227 | IspOH; 3 | Suspension | 1.57 |
| 47 | BDP; 0.1 | Ex. 20; 1 | 227 | EtOH; 1 | Solution | 2.10 |
| 48 | BDP; 0.1 | Ex. 20; 1 | 227 | EtOH; 8 | Solution | 2.42 |
| 49 | BDP; 0.1 | Ex. 1; 1 | 134a | EtOH; 9 | Solution | 2.02 |
| 50 | BDP; 0.1 | Ex. 1; 1 | 227 | EtOH; 8 | Solution | 2.64 |
| 51 | BTX; 0.2 | Ex. 16; 0.3 | 227 | 0 | Solution | * |
| 52 | BTX; 0.2 | Ex. 17; 0.8 | 227 | 0 | Suspension | * |
| 53 | BTX; 0.2 | Ex. 14; 2.2 | 227 | EtOH; 8 | Solution | 2.53 |
| 54 | BTX; 0.2 | Ex. 15; 2.9 | 227 | EtOH; 8 | Solution | * |
| 55 | BTX; 0.2 | Ex. 16; 3.1 | 227 | EtOH; 8 | Solution | 3.39 |
| 56 | BTX; 0.2 | Ex. 17; 0.6 | 227 | EtOH; 8 | Suspension | * |
| 57 | BTX; 0.1 | Ex. 18; 2.0 | 227 | EtOH; 8 | Solution | 2.44 |
| 58 | Albuterol $SO_4$; 0.2 | Ex. 15; 2.9 | 227 | EtOH; 4 | Suspension | 3.54 |
| 59 | BTX; 0.3 | Ex. 21; 3.0 | 227 | EtOH; 8 | Solution | 3.29 |
| 60 | BTX; 0.2 | Ex. 21; 2.0 | 227 | EtOH; 1 | Solution | 2.85 |

*data not collected

These results show a variety of PHAs are capable of being formulated with a variety of classes of drugs into both solution and suspension formulations. These formulations were capable of generating microparticles composed of PHA and drug with mass median aerodynamic diameters suitable for inhalation.

The foregoing detailed description and examples have been given for clarity of understanding only. No unnecessary limitations are to be understood therefrom. The invention is not limited to the exact details shown and described, for variations apparent to those skilled in the art are intended to be included within the invention defined by the claims. The complete disclosures of all patents, patent documents, and publications listed herein are incorporated by reference, as if each were individually incorporated by reference.

What is claimed is:

1. A medicinal aerosol solution formulation, comprising:
   (a) a biocompatible polymer substantially completely dissolved in the formulation; the biocompatible polymer comprising at least one chain of units of the formula —[X—$R^1$—C(O)]— wherein:
   (i) each $R^1$ is an independently selected organic group that links the —X— group to the carbonyl group; and
   (ii) each X is independently oxygen, sulfur, or catenary nitrogen;
   (b) a propellant selected from the group consisting of a chlorofluorocarbon, a hydrochlorofluorocarbon, a hydrofluorocarbon, or a mixture thereof; and
   (c) a drug substantially completely dissolved in the formulation in a therapeutically effective amount.

2. The formulation of claim 1, wherein the formulation is suitable for nasal and/or oral inhalation.

3. The formulation of claim 2 wherein each X is independently oxygen or catenary nitrogen.

4. The formulation of claim 3 wherein each X is oxygen.

5. The formulation of claim 4 wherein the biocompatible polymer is biodegradable.

6. The formulation of claim 1 wherein the biocompatible polymer is biodegradable.

7. The formulation of claim 6 wherein the biodegradable polymer has a number-average molecular weight of no greater than about 1500.

8. The formulation of claim 7 wherein the biodegradable polymer has a number-average molecular weight of no greater than about 1200.

9. The formulation of claim 7 wherein the biodegradable polymer has a number-average molecular weight of no greater than about 800.

10. The formulation of claim 7 wherein the biodegradable polymer has a number-average molecular weight of between 350 and 1500.

11. The formulation of claim 1 wherein the biocompatible polymer is capped on at least one end by a group that contains at least one hydrogen atom capable of hydrogen bonding.

12. The formulation of claim 1 wherein the biocompatible polymer is capped on at least one end by an ionic group.

13. The formulation of claim 1 wherein the biocompatible polymer is capped on at least one end by a group that contains no hydrogen atoms capable of hydrogen bonding.

14. The formulation of claim 13 wherein the biocompatible polymer is capped on at least one end by an organocarbonyl group.

15. The formulation of claim 14 wherein the biocompatible polymer is capped on at least one end by an acetyl group.

16. The formulation of claim 1 wherein the biocompatible polymer has a polydispersity of less than about 1.8.

17. The formulation of claim 1 wherein the biocompatible polymer has a polydispersity of less than about 1.4.

18. The formulation of claim 1 wherein the biocompatible polymer has a polydispersity of less than about 1.2.

19. The formulation of claim 18 wherein the biocompatible polymer has a number-average molecular weight of no greater than about 1500.

20. The formulation of claim 17 wherein the biocompatible polymer has a number-average molecular weight of no greater than about 1200.

21. The formulation of claim 16 wherein the biocompatible polymer has a number-average molecular weight of no greater than about 800.

22. The formulation of claim 1 further comprising a cosolvent.

23. The formulation of claim 22 wherein the cosolvent is selected from the group consisting of ethanol, isopropanol, acetone, ethyl lactate, dimethyl ether, menthol, tetrahydrofuran, and ethyl acetate.

24. The formulation of claim 23 wherein the cosolvent is ethanol.

25. The formulation of claim 1 wherein each $R^1$ is a straight chain, branched chain, or cyclic organic group containing 1–6 carbon atoms optionally containing carbonyl groups, oxygen atoms, thiol groups, or catenary nitrogen atoms.

26. The formulation of claim 25 wherein each $R^1$ is a straight chain alkylene or alkenylene group containing 1–6 carbon atoms optionally containing carbonyl groups, oxygen atoms, thiol groups, or fully substituted catenary nitrogen atoms, wherein the nitrogen substituents are free of nucleophilic or hydrogen-donor hydrogen bonding functional groups.

27. The formulation of claim 1 wherein the biocompatible polymer chain comprises units derived from one or more precursor hydroxyacids.

28. The formulation of claim 27 wherein the biocompatible polymer chain comprises units derived from one or more α-hydroxyacids.

29. The formulation of claim 27 wherein the biocompatible polymer chain comprises units derived from one or more precursors selected from the group consisting of glycolic acid, trimethylene carbonate, hydroxybutyric acids, p-dioxanone, L-lactic acid, and D-lactic acid.

30. The formulation of claim 29 wherein the biocompatible polymer chain comprises units derived from lactic acid and has an average chain length of about 3–25 of said units.

31. The formulation of claim 30 wherein the biocompatible polymer chain comprises units derived from lactic acid and has an average chain length of about 5–16 of said units.

32. The formulation of claim 1 wherein the biocompatible polymer has an average chain length of no greater than about 70 of said units.

33. The formulation of claim 1 wherein the biocompatible polymer has an average chain length of about 3–25 of said units.

34. The formulation of claim 1 wherein the formulation comprises about 0.01–25 parts by weight of the biocompatible polymer based on 100 parts of the formulation.

35. The formulation of claim 1 wherein the propellant comprises 1,1,1,2-tetrafluoroethane, 1,1,1,2,3,3,3-heptafluoropropane, or a mixture thereof.

36. The formulation of claim 1 wherein the drug is selected from the group consisting of antiallergics, analgesics, bronchodilators, antihistamines, antiviral agents, antibiotics, anti-inflammatories, immunomodulators, peptides, and steroids.

37. The formulation of claim 2 wherein the drug is selected from the group consisting of adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof.

38. The formulation of claim 2 in an aerosol canister equipped with a metered dose valve.

39. The formulation of claim 1 wherein the drug exhibits increased solubility in the propellant due to the biocompatible polymer.

40. The formulation of claim 1 wherein the drug exhibits increased chemical stability due to the biocompatible polymer.

* * * * *

UNITED STATES PATENT AND TRADEMARK OFFICE
CERTIFICATE OF CORRECTION

PATENT NO. : 6,416,742 B1
DATED : July 9, 2002
INVENTOR(S) : Stefely, James S.

It is certified that error appears in the above-identified patent and that said Letters Patent is hereby corrected as shown below:

Title page,
Item [56], References Cited, U.S. PATENT DOCUMENTS, "5,633,022" should read -- 5,633,002 --;
FOREIGN PATENT DOCUMENTS, delete "3/1986", should read -- 2/1986 --;
OTHER PUBLICATIONS, "M. Asano et al.," reference, "luteninzing" should read -- luteinizing --; "V.A. Philip et al.," reference, "Inahler" should read -- Inhaler --; and "H. Sato et al.," reference, after the word "Bull.," -- 19, -- should be inserted.

Column 3,
Line 21, insert a -- . -- after the word "thereof".

Column 6,
Line 4, insert -- (MDI). -- after the word "inhaler".

Column 15,
Line 31, please delete the "0" after "100º".

Column 21,
Line 30, please delete "Tg, Tm" and insert in place thereof -- $T_g$ $T_m$ --.

Column 23,
Line 17, please delete "fritter" and insert in place thereof -- filter --.
Line 18, please delete "flitted" and insert in place thereof -- fritted --.

Column 29,
Line 52, insert -- = -- following "Mn".

UNITED STATES PATENT AND TRADEMARK OFFICE
CERTIFICATE OF CORRECTION

PATENT NO.   : 6,416,742 B1
DATED        : July 9, 2002
INVENTOR(S)  : Stefely, James S.

It is certified that error appears in the above-identified patent and that said Letters Patent is hereby corrected as shown below:

Column 33,
Line 10, table 4, "1000" should read -- 100 --.

Signed and Sealed this

Twenty-seventh Day of April, 2004

JON W. DUDAS
*Acting Director of the United States Patent and Trademark Office*